(12) United States Patent
Lee et al.

(10) Patent No.: US 7,708,758 B2
(45) Date of Patent: May 4, 2010

(54) SURGICAL INSTRUMENT

(75) Inventors: Woojin Lee, Hopkinton, MA (US);
Andres Chamorro, Natick, MA (US);
Richard Ross, Montgomery Center, VT (US)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 360 days.

(21) Appl. No.: 11/605,694

(22) Filed: Nov. 28, 2006

(65) Prior Publication Data
US 2008/0046000 A1 Feb. 21, 2008

Related U.S. Application Data

(60) Provisional application No. 60/838,059, filed on Aug. 16, 2006.

(51) Int. Cl.
*A61B 17/00* (2006.01)
(52) U.S. Cl. .................................................... 606/205
(58) Field of Classification Search .................. 403/90; 606/139–149, 205–209
See application file for complete search history.

(56) References Cited

U.S. PATENT DOCUMENTS

| | | | |
|---|---|---|---|
| 2,028,635 A | 1/1936 | Wappler | |
| 2,507,710 A | 5/1950 | Grosso | |
| 2,790,437 A | 4/1957 | Moore | |
| 3,557,780 A | 1/1971 | Sato | |
| 3,858,577 A | 1/1975 | Bass et al. | |
| 3,895,636 A | 7/1975 | Schmidt | |
| 4,483,562 A | 11/1984 | Schoolman | |
| 4,688,554 A | 8/1987 | Habib | |
| 4,728,020 A | 3/1988 | Green et al. | |
| 4,763,669 A | 8/1988 | Jaeger | |
| 4,872,456 A | 10/1989 | Hasson | |
| 4,880,015 A | 11/1989 | Nierman | |
| 4,944,093 A | 7/1990 | Falk | |

(Continued)

FOREIGN PATENT DOCUMENTS

EP 0 095 970 A2 12/1983

(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs.

(Continued)

*Primary Examiner*—Todd E Manahan
*Assistant Examiner*—Eric Blatt
(74) *Attorney, Agent, or Firm*—David M. Driscoll, Esq.

(57) ABSTRACT

The surgical instrument includes a distal tool, an elongated shaft that supports the distal tool, and a proximal handle or control member, where the tool and the handle are coupled to the respective distal and proximal ends of the elongated shaft via distal and proximal bendable motion members. Actuation means extends between said distal and proximal members whereby any deflection of said control handle with respect to said elongated instrument shaft causes a corresponding bending of said distal motion member for control of said working member. The proximal bendable member comprises a ball and socket assembly supported between the handle and instrument shaft and constructed and arranged for three dimensional motion.

88 Claims, 9 Drawing Sheets

U.S. PATENT DOCUMENTS

| | | | |
|---|---|---|---|
| 4,944,741 A | 7/1990 | Hasson | |
| 4,945,920 A | 8/1990 | Clossick | |
| 5,002,543 A | 3/1991 | Bradshaw et al. | |
| 5,042,707 A | 8/1991 | Taheri | |
| 5,209,747 A | 5/1993 | Knoepfler | |
| 5,254,130 A * | 10/1993 | Poncet et al. | 606/206 |
| 5,271,381 A | 12/1993 | Ailinger et al. | |
| 5,273,026 A | 12/1993 | Wilk | |
| 5,275,608 A | 1/1994 | Forman et al. | |
| 5,314,424 A | 5/1994 | Nicholas | |
| 5,330,502 A | 7/1994 | Hassler et al. | |
| 5,344,428 A | 9/1994 | Griffiths | |
| 5,383,880 A | 1/1995 | Hooven | |
| 5,386,818 A | 2/1995 | Schneebaum et al. | |
| 5,395,367 A | 3/1995 | Wilk | |
| 5,405,344 A | 4/1995 | Williamson et al. | |
| 5,433,721 A | 7/1995 | Hooven et al. | |
| 5,441,494 A | 8/1995 | Ortiz | |
| 5,454,827 A | 10/1995 | Aust et al. | |
| 5,501,654 A | 3/1996 | Failla et al. | |
| 5,520,678 A | 5/1996 | Heckele et al. | |
| 5,599,151 A | 2/1997 | Daum et al. | |
| 5,618,294 A | 4/1997 | Aust et al. | |
| 5,643,294 A | 7/1997 | Tovey et al. | |
| 5,702,408 A | 12/1997 | Wales et al. | |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,899,425 A | 5/1999 | Corey Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,928,263 A | 7/1999 | Hoogeboom | |
| 5,938,678 A | 8/1999 | Zirps et al. | |
| 5,944,713 A | 8/1999 | Schuman | |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,551,238 B2 | 4/2003 | Staud | |
| 6,623,424 B2 | 9/2003 | Hayakawa et al. | |
| 6,638,214 B2 | 10/2003 | Akiba | |
| 6,641,316 B1 * | 11/2003 | Goldstein et al. | 400/489 |
| 6,656,195 B2 | 12/2003 | Peters et al. | |
| 6,666,854 B1 | 12/2003 | Lange | |
| 6,752,756 B2 | 6/2004 | Lunsford et al. | |
| 6,761,717 B2 | 7/2004 | Bales et al. | |
| 7,090,637 B2 | 8/2006 | Danitz | |
| 7,147,650 B2 | 12/2006 | Lee | |
| 7,320,700 B2 * | 1/2008 | Cooper et al. | 606/205 |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0149338 A1 | 8/2003 | Francois et al. | |
| 2003/0216618 A1 | 11/2003 | Arai | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0107667 A1 | 5/2005 | Danitz et al. | |
| 2005/0228440 A1 | 10/2005 | Brock et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0195097 A1 | 8/2006 | Evans et al. | |
| 2006/0206101 A1 | 9/2006 | Lee | |
| 2006/0270909 A1 | 11/2006 | Davis et al. | |
| 2007/0250110 A1 | 10/2007 | Lu et al. | |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Ryoichi Nakamura et al., Multi-DOF Manipulator System for Laparoscopic Surgery, 8 pgs.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

* cited by examiner

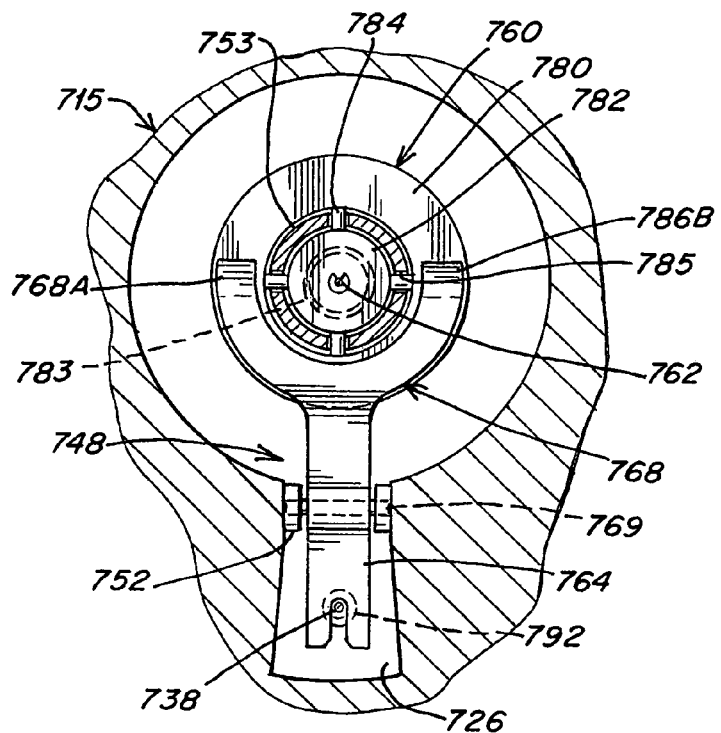
Fig. 4
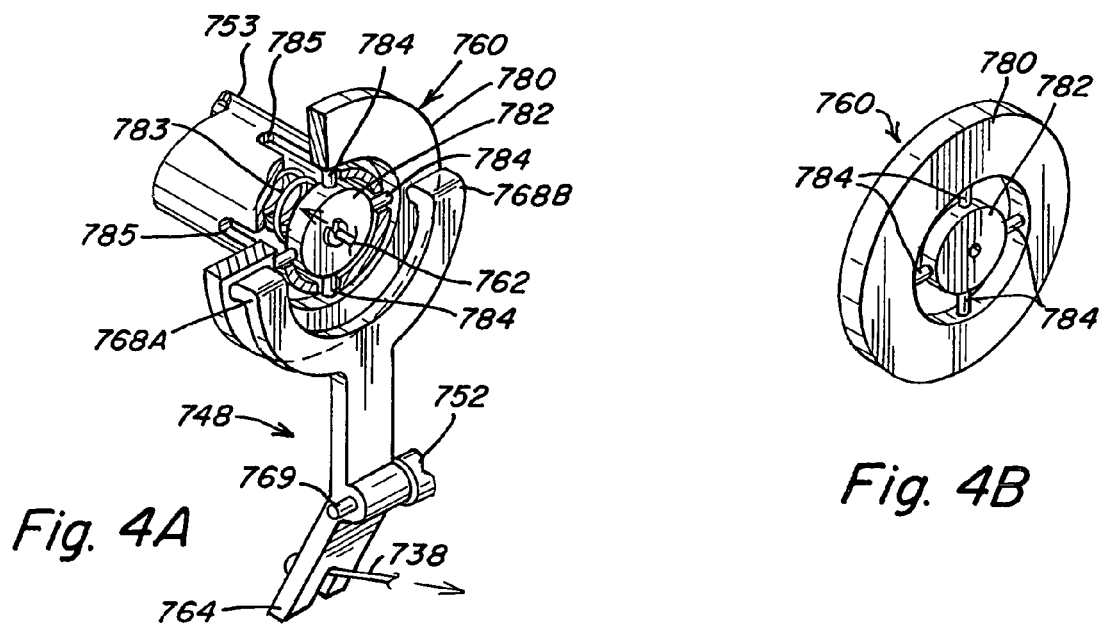
Fig. 4A
Fig. 4B

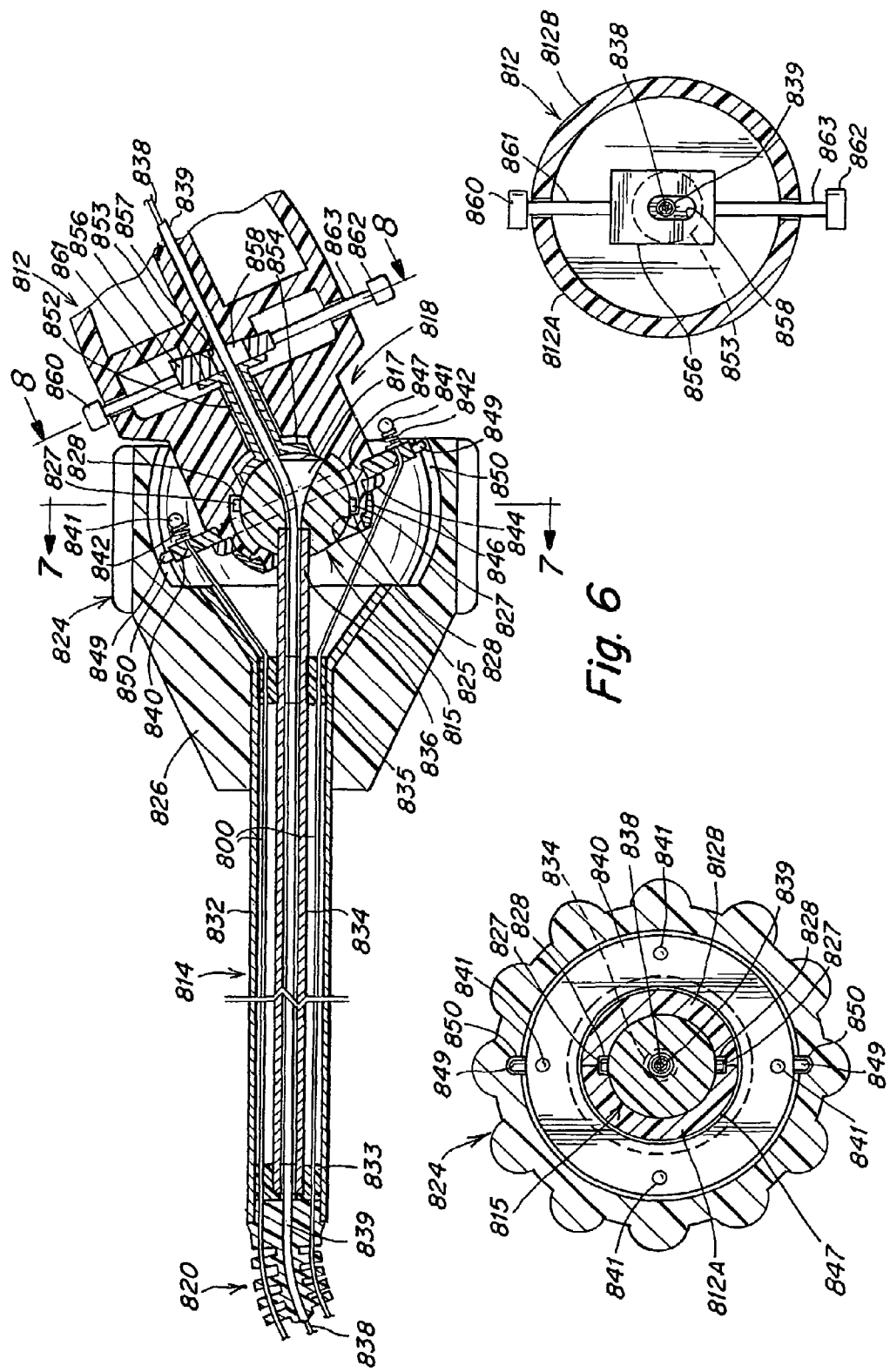

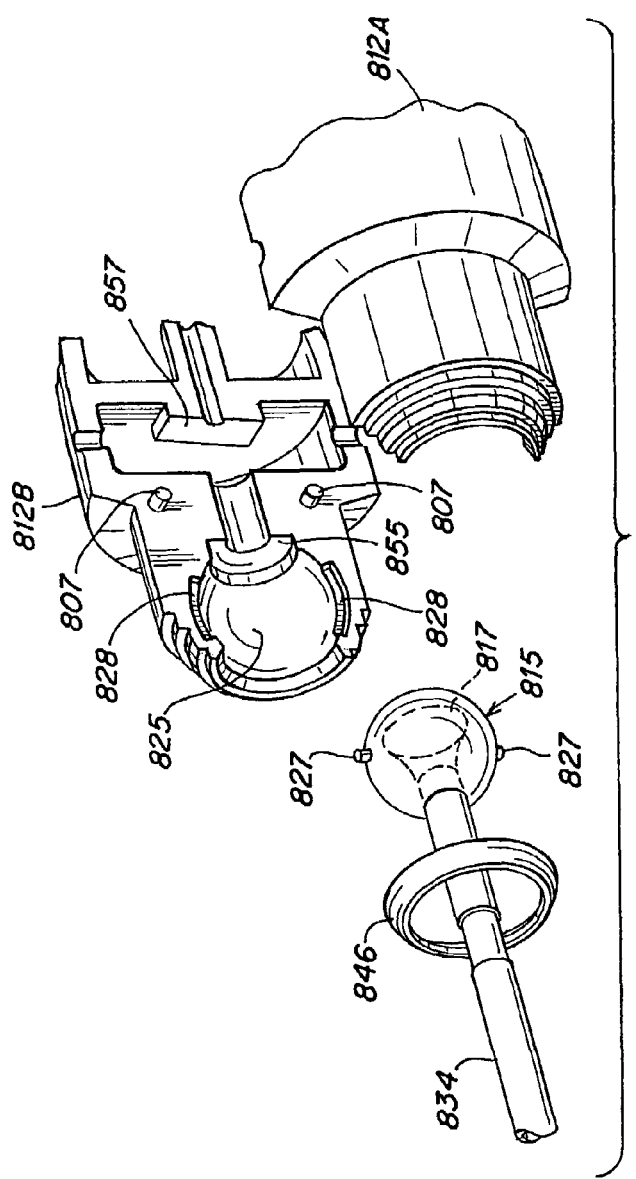
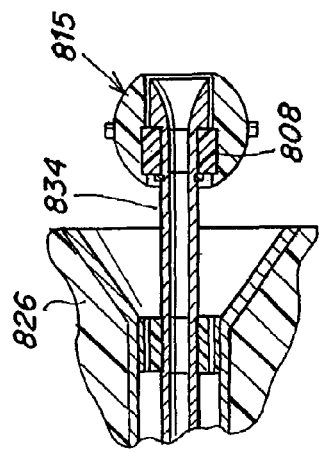
Fig. 9
Fig. 10

SURGICAL INSTRUMENT

RELATED APPLICATION

Priority for this application is hereby claimed under 35 U.S.C. § 119(e) to commonly owned U.S. Provisional Patent Application No. 60/838,059 which was filed on Aug. 16, 2006. The content of all of the aforementioned application is hereby incorporated by reference herein in its entirety.

TECHNICAL FIELD

The present invention relates in general to surgical instruments, and more particularly to manually-operated surgical instruments that are intended for use in minimally invasive surgery or other forms of surgical or medical procedures or techniques. The instrument described herein is primarily for laparoscopic or endoscopic procedures, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the locations of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation. Also, existing instruments of this type do not provide an effective way to hold the instrument in a particular position. Moreover, existing instruments require the use of both hands in order to effectively control the instrument.

Accordingly, an object of the present invention is to provide an improved laparoscopic or endoscopic surgical instrument that allows the surgeon to manipulate the tool end of the surgical instrument with greater dexterity.

Another object of the present invention is to provide an improved surgical or medical instrument that has a wide variety of applications, through incisions, through natural body orifices or intraluminally.

A further object of the present invention is to provide an improved medical instrument that is characterized by the ability to lock the instrument in a particular position.

Another object of the present invention is to provide a locking feature that is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Still another object of the present invention is to provide an improved medical instrument that can be effectively controlled with a single hand of the user.

Still another object of the present invention is to provide an improved medical instrument that is characterized by the ability to lock the position of the instrument in a pre-selected position while enabling rotation of the tip of the instrument while locked.

SUMMARY OF THE INVENTION

In accordance with the present invention there is provided a medical instrument that comprising, a proximal control handle; a distal work member; a proximal movable member controlled from the proximal control handle; a distal movable member controlled from the proximal movable member to provide controlled movement of the distal work member from the proximal control handle; an instrument shaft that intercouples the proximal and distal movable members; and actuation means coupled between the movable members. The proximal movable member comprises a ball and socket assembly supported between the handle and instrument shaft and constructed and arranged for three dimensional motion.

In accordance with other aspects of the present invention the medical instrument may further include a locking member supported from the proximal control handle and having locked and unlocked states; the locking member in the unlocked state enabling control of the distal work member from the proximal control handle via the movable members; the locking member, in said locked state, holding the movable members in a desired fixed position; the locking member, in the locked state, fixes the position of the proximal movable member; the distal movable members may comprise a unibody structure; the ball and socket assembly may include a ball supported from the instrument shaft, a socket defined in the handle and an anchor ring rotatably supported at the handle; the actuation means may comprise a plurality of cables that are supported at proximal ends by the anchor ring; the ball may have pins that ride in slots in the socket; a rotation control member and a piston assembly may couple between the handle and rotation control member; the piston assembly may further include pistons, a ring on the rotation control member, links that pivotally connect between the ring and pistons and a locking knob for holding a position of the pistons; the piston assembly may further comprise a rotatable cage supported by the handle, sliders supported by the cage and links coupled between the sliders and the rotation control member; a follower on the handle and including a rider, a sphere for supporting the rider and an anchor ring rotatably supported on the rider; a locking member having a split ball and a wedge member movable into the split ball to lock the position of the proximal moveable member; a rotation control member adjacent the proximal control handle for controlling the distal work member to rotate about a distal work member axis; the actuation means may comprise a set of cables that couple between said moveable members and further including a cable retainer supported by the handle and for retaining proximal ends of the cables; the handle may comprise a pistol grip handle that includes a base and a top section that defines a spherical socket that supports the ball and with the ball supporting the proximal moveable member; and the proximal moveable member may comprise a unitary bendable member and further including a rotatable control member in line with the proximal bendable member.

In another embodiment of the present invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between said movable members and a rotation ball and wherein the control handle comprises a base and a top section that defines a spherical socket that supports the rotation ball for three dimensional pivoting therein.

In accordance with still other aspects of the present invention the proximal moveable member may comprise a proximal bendable member that is supported by the rotation ball; a rotation control member may be supported in line with the proximal bendable member for controlling the three dimensional pivoting; the rotation control member may control the three dimensional pivoting, as well as a rotation about a longitudinal axis of the proximal bendable member so as to control the rotation of the tool about its distal tool axis; a pivot control member at the proximal end of said proximal bendable member may control the three dimensional pivoting; the pivot control member also may control rotation of the instrument shaft; and preferably including a locking means that is manually operable by a user and that locks the ball in the socket.

In accordance with another embodiment of the present invention there is provided, in a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, and cable actuation means disposed between the movable members, a method of controlling the tool from the handle by means of a control element comprising pivoting the control element to control the positioning of the tool in three dimensions and to control the rotational orientation of the tool by rotating the instrument shaft. This method may also include providing a ball and socket as part of the proximal moveable member and controlling the control element so as to pivot the ball relative to the socket.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which:

FIG. 4 is a cross-sectional view taken along line 4-4 of FIG. 3;

FIG. 4A is fragmentary perspective view of part of the cable actuation mechanism used in the instrument shown in FIG. 1;

FIG. 4B is a perspective view of the transfer disc arrangement used in the mechanism of FIG. 4A;

FIG. 6 is a fragmentary cross-sectional plan view of an alternate embodiment of the instrument;

FIG. 7 is a cross-sectional view taken along line 7-7 of FIG. 6;

FIG. 8 is a cross-sectional view taken along line 8-8 of FIG. 6;

FIG. 9 is an exploded perspective view of part of the embodiment shown in FIGS. 6-8;

FIG. 10 is a fragmentary cross-sectional view of an alternate embodiment of the support between the shaft and ball;

DETAILED DESCRIPTION

The instrument of the present invention may be used to perform minimally invasive procedures. "Minimally invasive procedure," refers herein to a surgical procedure in which a surgeon operates through small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen or vessel, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thoracic, transvaginal, orthopedic and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

Figure 1:
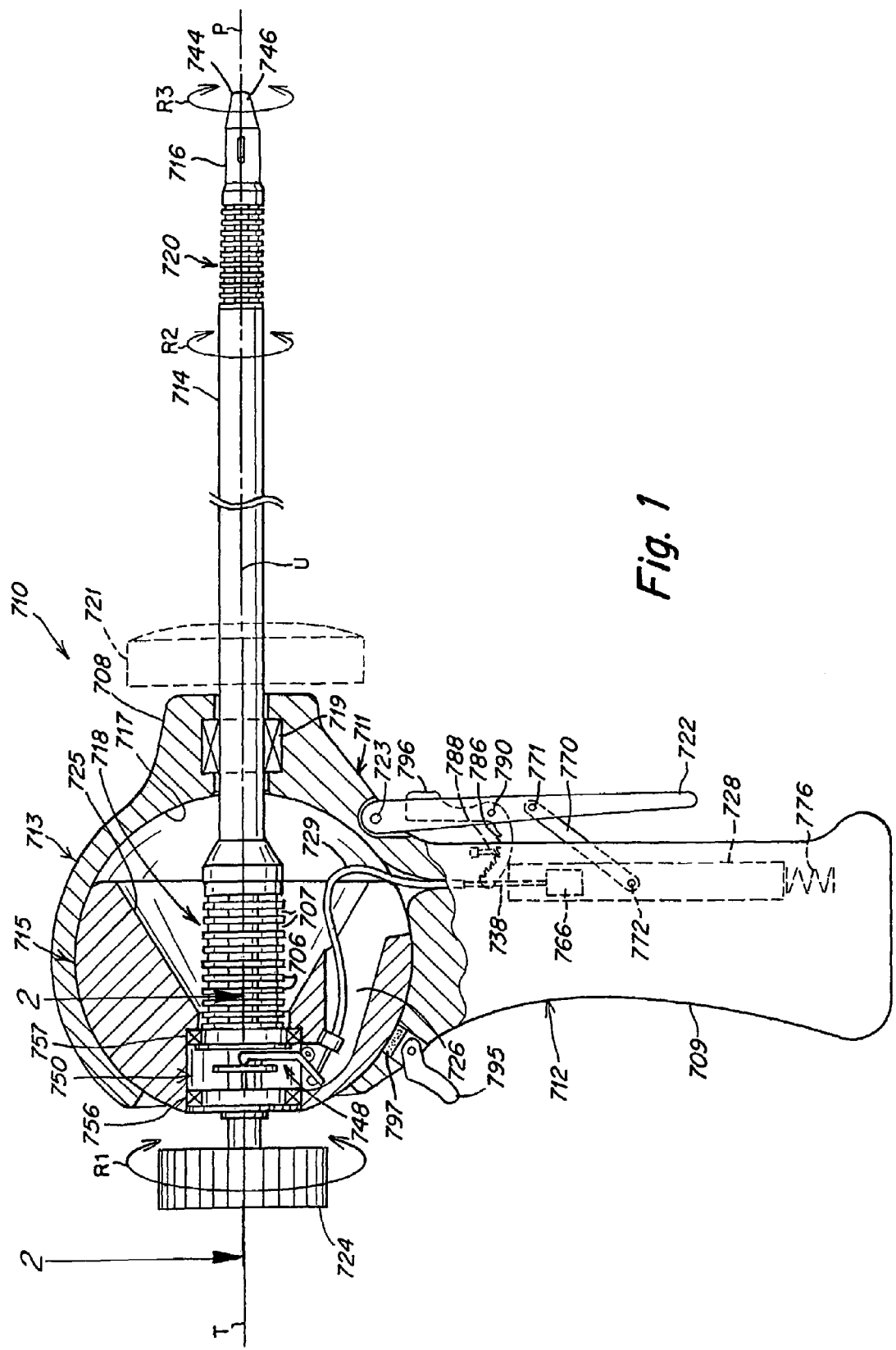
FIG. 1 is a partially cut-away schematic side elevation view of a first embodiment of the surgical instrument of the present invention.

FIG. 1 is a schematic side view of a one embodiment of the surgical instrument 710 of the present invention. In this surgical instrument both the tool and handle motion members or bendable members are capable of bending in any direction. They are interconnected via cables in such a way that a bending action at the proximal member provides a related bending at the distal member. The proximal bending is controlled by a motion, pivoting or deflection at the rotation control member 724 by a user of the instrument. In other words the surgeon grasps the pistol grip handle and once the instrument is in position any motion (deflection) at the rotation knob immediately controls the proximal bendable member 718 which, in turn, via cabling controls a corresponding bending or deflection at the distal bendable member 720. This action, in turn, controls the positioning of the distal tool 716. Refer to the separate positions illustrated FIGS. 1 and 5 for a depiction of this motion.

The proximal member 718 is preferably generally larger than the distal member 720, as illustrated in, for example, FIG. 1, so as to provide enhanced ergonomic control. In one version in accordance with the invention there may be provided a bending action in which the distal bendable member bends in the same direction as the proximal bendable member. In an alternate embodiment the bendable, turnable or flexible members may be arranged to bend in opposite directions by rotating the actuation cables through 180 degrees, or could be controlled to bend in virtually any other direction depending upon the relationship between the distal and proximal support points for the cables.

It should be noted that the amount of bending motion produced at the distal bending member is determined by the dimension of the proximal bendable member in comparison to that of the distal bendable member. In the embodiment described the proximal bendable member is generally larger than the distal bendable member, and as a result, the magnitude of the motion produced at the distal bendable member is greater than the magnitude of the motion at the proximal bendable member. The proximal bendable member can be bent in any direction (about 360 degrees) controlling the distal bendable member to bend in either the same or an opposite direction, but in the same plane at the same time. Also, the surgeon is able to bend and roll the instrument's tool about its longitudinal axis at any orientation simply by rolling or rotating the axial rotation knob 724.

In this description reference is made to bendable members. These members may also be referred to as turnable members or flexible members. In the descriptions set out herein, terms such as "bendable section," "bendable segment," "bendable motion member," or "turnable member" refer to an element of the instrument that is controllably bendable in comparison to an element that is pivoted at a joint. The bendable elements of the present invention enable the fabrication of an instrument that can bend in any direction without any singularity and that is further characterized by a ready capability to bend in any direction, all preferably with a single unitary or uni-body structure. A definition of a "unitary" or "uni-body" structure is:—a structure that is constructed only of a single integral member and not one that is formed of multiple assembled or mated components—.

A definition of these bendable motion members is—an instrument element, formed either as a controlling means or a controlled means, and that is capable of being constrained by tension or compression forces to deviate from a straight line to a curved configuration without any sharp breaks or angularity—. Bendable members may be in the form of unitary structures, such as shown herein in FIG. 1 or may take on other forms such as shown in FIGS. 6-15. For other forms of bendable members refer to co-pending application Ser. No. 11/505,003 filed on Aug. 16, 2006, Ser. No. 11/523,103 filed on Sep. 19, 2006 and Ser. No. 11/528,134 filed on Sep. 27, 2006 all of which are hereby incorporated by reference herein in their entirety.

FIG. 1 shows a first embodiment of the instrument of the present invention. FIG. 1 depicts the surgical instrument 710 in position, as may occur during a surgical procedure. For example, the instrument may be used for laparoscopic surgery through an abdominal wall. For this purpose there is usually provided an insertion site at which there is disposed a cannula or trocar. The shaft 714 of the instrument 710 is adapted to pass through the incision so as to dispose the distal end of the instrument at an operative site. The end effector 716 shown in FIG. 1 may be considered as at such an operative site. FIG. 1 also depicts the rolling motion that can be carried out with the instrument of the present invention. This can occur by virtue of the rotation of the rotation knob 724 relative to the handle 712 about axis T. This is illustrated in FIG. 1 by the circular arrow R1. When the rotation knob 724 is rotated, in either direction, this causes a corresponding rotation of the instrument shaft 714. This is depicted in FIG. 1 by the rotational arrow R2. This same motion also causes a rotation of the end effector 716 about axis P as illustrated by the rotational arrow R3. It is noted in FIG. 1 where the instrument is arranged in a straight position that the axes T and P coincide. See also FIG. 5 where the tip of the instrument is shown extending along axis P at an angle B2. If rotation occurs in the position of FIG. 35, whether the instrument is locked or unlocked, then the tip (end effector) motion is rotation about the axis P.

Any rotation of the rotation knob 724 while the instrument is locked (or unlocked) maintains the instrument tip at the same angular position, but rotates the orientation of the tip (tool). For a further explanation of the rotational feature refer to co-pending application Ser. No. 11/302,654, filed on Dec. 14, 2005, particularly FIGS. 25-28, which is hereby incorporated by reference in its entirety.

Figure 5:
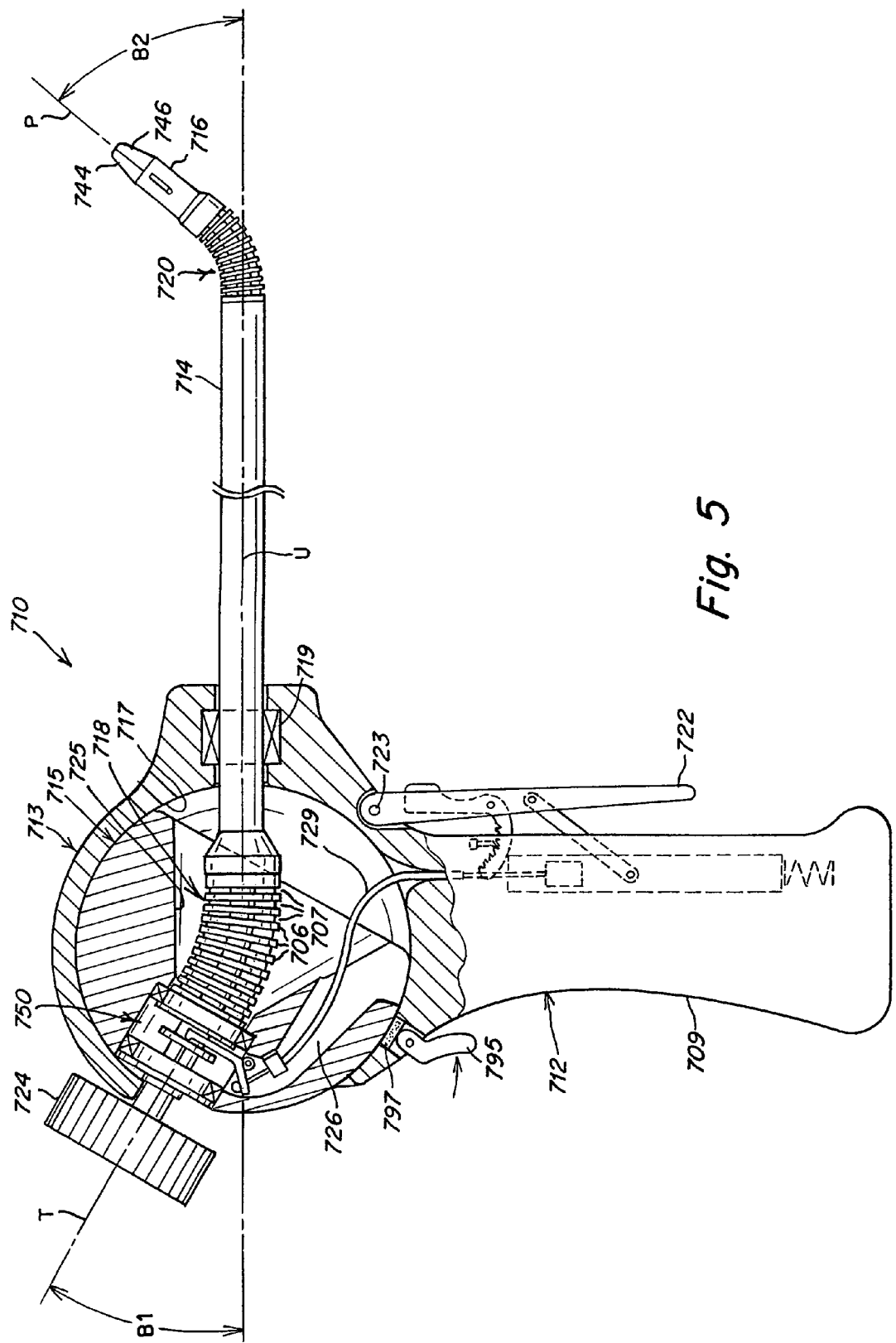
FIG. 5 is a partially cut-away schematic side elevation view of the instrument of FIG. 1 with the instrument being manually controlled to bend and rotate the end effector.

In FIG. 1 the handle 712 is shown at a neutral position in which the axis T of the rotation knob 724 is in line with the axis U of the instrument shaft 714. In that position the distal bendable member 720 and end effector 716 are also in line. FIG. 5, on the other hand, shows the instrument bent by deflecting, pivoting or tilting the rotation knob 724 upwardly to, in turn, control the bending of the proximal bendable member 718. The rotation knob 724, in FIG. 5, is shown tilted along axis T at an angle B1 to the instrument shaft longitudinal center axis U. This tilting, deflecting or bending may be considered as in the plane of the paper, although it is understood that the bending can also be in and out of the plane of the paper.

By means of the cabling 700 this action causes a corresponding bend at the distal bendable member 720 to a position wherein the tip is directed along axis P and at an angle B2 to the instrument shaft longitudinal center axis U. The bending at the proximal bendable member 718 is controlled by the surgeon primarily from the tilting of the rotation knob which can be tilted up and down or into and out of the paper in FIG. 5. This manipulation directly controls the bending at the distal bendable member, via bend control cables that connect at their opposite ends to the respective distal and proximal bendable members.

Thus, the control at the handle is used to bend the instrument at the proximal motion member to, in turn, control the positioning of the distal motion member and tool. The "position" of the tool is determined primarily by this bending or motion action and may be considered as the coordinate location at the distal end of the distal motion member. Actually, one may consider a coordinate axis at both the proximal and distal motion members as well as at the instrument tip. This positioning is in three dimensions. The "orientation" of the tool, on the other hand, relates to the rotational positioning of the tool about the illustrated distal tip axis (see axis P in FIG. 5).

The knob 724 thus may be considered as having the dual function use as a means for controlling the bending action, referred to herein as "pivoting" for controlling the positioning of the end effector, as well as a means for controlling the orientation of the end effector by a rotation function for positioning of the end effector about the distal tip axis.

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

The surgical instrument of FIG. 1 shows a first embodiment of a surgical instrument 710 according to the invention in use, such as inserted through a cannula or trocar at an insertion site through a patient's skin. Many of the components described herein, such as the instrument shaft 714, end effector 716, distal bending member 720, and proximal bending member 718 are similar to and interact in the same manner as like instrument components described in the co-pending U.S. application Ser. No. 11/185,911 filed on Jul. 20, 2005 and hereby incorporated by reference herein in its entirety. Also incorporated by reference in their entirety are U.S. application Ser. No. 10/822,081 filed on Apr. 12, 2004; U.S. application Ser. No. 11/242,642 filed on Oct. 3, 2005 and U.S. application Ser. No. 11/302,654 filed on Dec. 14, 2005.

In the first embodiment described herein it is noted that the instrument uses a handle that is a pistol grip type and that supports the instrument shaft 714 with the shaft rotatable in the handle. The distal end of the instrument shaft supports the distal bendable member 720 and the end effector 716. The control of the distal bendable member is from the proximal bendable member via cabling 700 that interconnects between the bendable members. The proximal bendable member 718 is housed in the handle, particularly at the spherically shaped top section 713 of the handle housing 711. This top section of the handle housing comprises a ball and socket arrangement in which the ball 715 is adapted for rotational support in the handle socket 717.

The proximal bendable member 718 is supported from the ball 715, as is the rotation knob 724. In this embodiment, rather than the handle directing the action of the proximal bendable member, the proximal bendable member is controlled primarily by pivoting or deflecting the ball 715 in three dimensions. The pivoting of the ball 715 is, in turn, controlled directly by the rotation knob 724. FIG. 1 shows the instrument with the rotation knob at an intermediate or neutral position in which the bendable members are essentially in line with each other. On the other hand, FIG. 5 illustrates the rotation knob having been tilted or pivoted upwardly at the illustrated angle B1. In this version the bend control cables 700 (see FIG. 2) are interconnected through the instrument shaft so that an upward motion of the rotation knob causes the distal bendable member to bend upwardly. This is carried out by twisting the cables through 180 degrees as they pass from one end to the other of the instrument shaft. If the cables are connected without being twisted through 180 degrees then an upward movement of the rotation knob causes a downward movement of the distal bendable member. Of course the rotation knob 724 can also be controlled to move in and out of the plane of the paper to control the distal bendable member to also move in and out of the plane of the paper.

As indicated previously in this embodiment the cabling within the instrument shaft is shown in a straight configuration such as illustrated in FIG. 1, and is shown in a bent condition in FIG. 5. The end effector or tool 716 is actuated by means of a jaw actuation means which is comprised primarily of the elongated lever 722 that is disposed adjacent to the base 709 of the pistol grip handle 712. The lever 722 is supported from the housing at the lever pivot pin 723. The closing of the lever 722 against the handle base 709, acts upon the slider 728 which is used to capture the very proximal end of the tool actuation cable 738. When the lever 722 is un-actuated (separated from the handle housing) this corresponds to the end effector jaws being in a fully open position. When the lever 722 closes, as shown in FIG. 1, this causes the slider 728 to move downward, and then the jaws 744 and 746 are moved toward a closed position. The jaw actuator cable 738 terminates at its respective ends at the bellcrank 748 and the rotation barrel 766 (see FIG. 1).

Within each of the bendable sections or bendable members 718 and 720 there may be provided a plastic tube. This includes a distal tube and a proximal tube. Both of these tubes may be constructed of a plastic such as polyethyletherkeytone (PEEK). The material of the tubes is sufficiently rigid to retain the cable 762 and yet is flexible enough so that it can readily bend with the bending of the bendable members 718 and 720. The tubes have a sufficient strength to receive and guide the cable, yet are flexible enough so that they will not kink or distort, and thus keep the cable in a proper state for activation, and also defines a fixed length for the cable. The tubes are longitudinally stiff, but laterally flexible. For further details of these bendable sections and tubes refer to the aforementioned co-pending application Ser. No. 11/185,911.

The control of the end effector 716 originates at the jaw actuator cable 738. As mentioned previously the very proximal end of the jaw actuator cable 738 is retained in the rotational barrel 766. The rotational barrel 766 is supported within the slider 728. The slider 728 is also provided with a slot that extends from the slider pocket and accommodates the link 770. The link 770 is the main means for actuating the slider 728 and, in turn, the actuator cable 738 from the lever 722.

The actuation link 770 is supported at one end from the lever 722 by means of the pivot pin 771. The opposite end of the link 770 is supported at another pin, referred to herein as slider pin 772. The pin 772 is retained for longitudinal movement in a slot (not shown) in the slider 728. FIGS. 1 and 5 show the respective pins 771 and 772 at the opposite ends of the link 770. FIGS. 1 and 5 also schematically illustrate the slider urged against the actuator spring 776. The spring 776 is disposed within a compartment of the slider 728. For further details of the lever and slider arrangement refer to the aforementioned Ser. No. 11/185,911. The arrangement may additionally include a return spring.

The lever 722 actuates the end effector 716 as it is pressed toward the handle body. The lever 722 operates with a ratchet and pawl arrangement with the lever capable of being depressed in ratcheted increments. This ratchet and pawl arrangement includes the ratchet 786 and pawl 788. To accommodate the ratchet 786, the slider 728 may be provided with an end dish out or cut out. The pawl 788 is retained by the handle 712. The ratchet 786 pivots at the pivot pin 790 and is provided with a series of ratchet teeth that can hold the ratchet in successive positions corresponding to successive degrees of closure of the end effector. A torsion spring (not shown) is preferably disposed partially about the pivot 790 and urges the ratchet teeth into contact with the pawl 788. The ratchet and pawl arrangement also includes an integral release means that is usually engageable by the surgeon's thumb. This is depicted in FIG. 1 by the release button 796. When a force is directed against the button 796 then this releases the ratchet and pawl arrangement and returns the lever 722 to its released position with the jaws fully opened. The pressing of the button 796 rotates the ratchet 786 out of engagement with the pawl 788.

FIG. 1 illustrates the instrument shaft 714 supported at the flange 708 of the handle. This support includes the bearing 719 that enables rotational support of the instrument shaft relative to the instrument handle. FIG. 1 also shows in dotted outline a possible alternate position of the rotation knob at 721. In that arrangement the knob is firmly attached to the outside of the instrument shaft so as to enable manual rotation thereof.

Reference is now made to the cabling that extends between the proximal and distal bendable members. This cabling is provided so that any bending at the proximal bendable member is converted into a corresponding bending at the distal bendable member. The bendable members that are described herein enable bending in all directions. In the preferred embodiment described herein, the distal bendable member is approximately ½ the diameter of the proximal bendable member as illustrated in FIG. 5. However, as indicated before other diameter relationships can be used depending upon the particular use of the instrument and the medical procedure in which it is being used. In one embodiment it is even possible that the distal bendable member is larger in diameter than the proximal bendable member.

Figure 2:
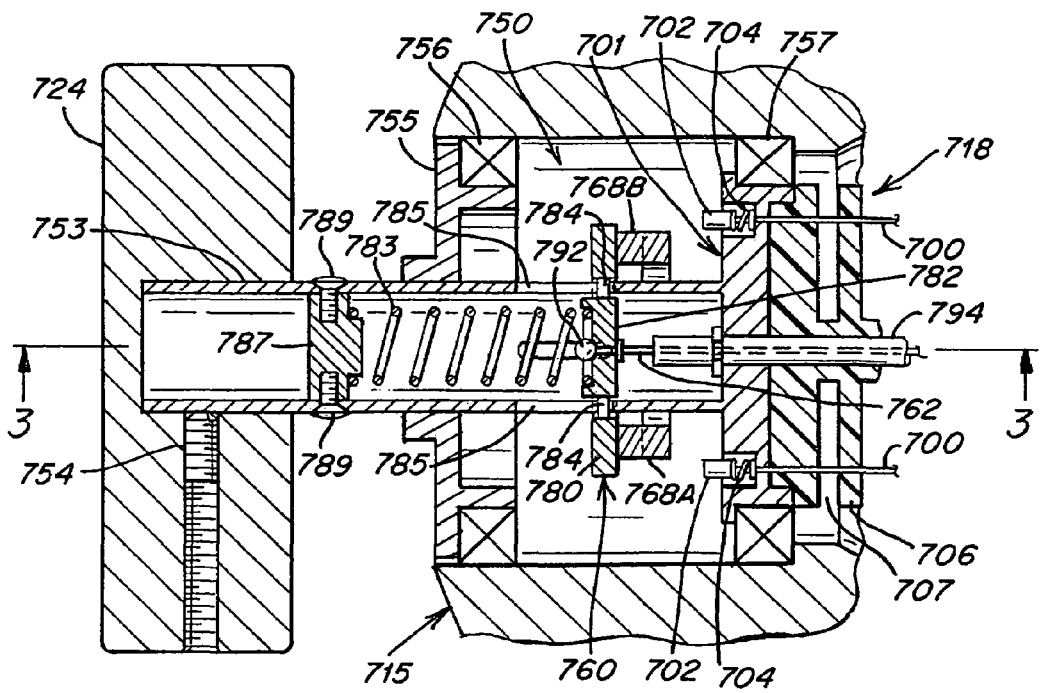
FIG. 2 is a cross-sectional view of the embodiment of the instrument shown in FIG. 1 and as taken along line 2-2 of FIG. 1.

The control between the proximal bendable member 718 and the distal flexible member 720 is carried out by means of the flex control cables 700. There may be provided four such cables. At the distal end of these cables they may connect to anchor at the most distal end of the distal bendable member. Cables 700 are retained at their proximal ends by cable end lugs 702, as shown in FIG. 2. Four springs 704 are retained between these end lugs 702 and a wall of the hub 701. Resilient pads may be substituted for the springs. Refer to FIG. 2 for an illustration of the end lugs 702, springs 704 and the hub 701 which is disposed at the very proximal end of the proximal bendable member. The springs 704 tension or take up the slack on the cables 700. Between the bendable members, the cables 700 may be guided by means of slots in spacers (not shown) that may be disposed along the support tube of the instrument shaft.

The construction of both of the bendable members may be a unitary slotted structure, as depicted in FIG. 1. For more details of the distal bendable member refer to the aforementioned Ser. No. 11/185,911 which illustrates the use of spaced discs that define slots and that may be interconnected by a rib arrangement that enables the bendable member to readily bend in any direction as controlled from the bend control cables that are attached to the distal bendable member and that are controlled from the proximal bendable member.

A partial cross-sectional view of the proximal bendable member 718 is shown in FIG. 2 including the spaced discs 706 that define therebetween the slots 707. The proximal bendable member preferably also includes interconnecting ribs between discs and that are preferably disposed at 60 degree intervals to provide effective three dimensional bending.

Referring again to FIGS. 1 and 5, the ball 715 is basically spherical in shape and is accommodated in a spherical socket 717. To allow assembly between the ball and the handle housing, the handle may be made in two parts that are assembled about the ball 715. The ball 715 also includes a conical cavity 725 in which the proximal bendable member is disposed. This conical cavity 725 provides an open space in which the proximal bendable member 718 can bend. In FIG. 1 the proximal bendable member 718 is shown at a middle area of the conical cavity, while in FIG. 5 the proximal bendable member 718 is shown in a bent condition and thus close to a wall of the cavity. In the position illustrated in FIG. 5 it is noted that the conical cavity 725 provides sufficient room to enable bending of the proximal bendable member 718.

Figure 3:
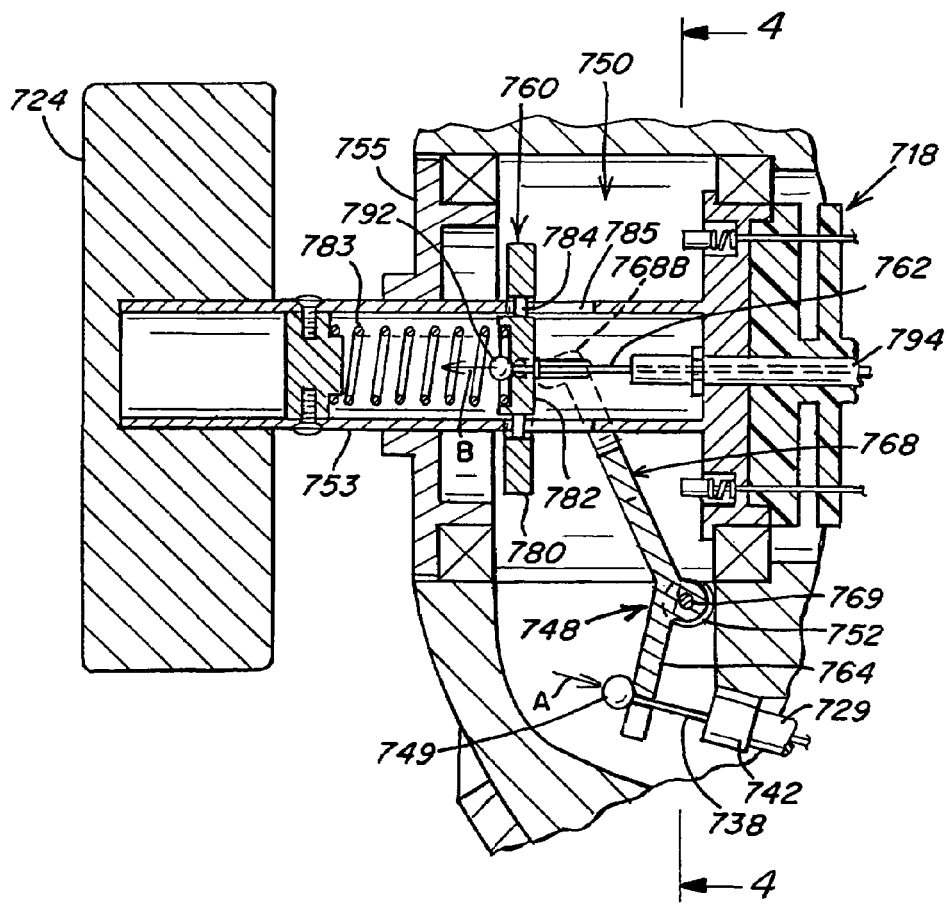
FIG. 3 is an enlarged cross-sectional view of the instrument shown in FIG. 1 and as taken along line 3-3 of FIG. 2.

The ball 715 also includes a slot 726 that accommodates the tool actuation cable 738. The tool actuation cable 738 is disposed in a sheath 729 that extends from just above the slider 728 to a position adjacent to the tool actuation assembly 750. Both ends of the sheath 729 are fixed in position with the tool actuation cable 738 moving therethrough as it is actuated. Refer to FIG. 3 where one end of the sheath 729 is shown at 742. FIG. 3 also illustrates the very end (ball end) of cable 738 at 749 attached to one leg of the bellcrank 748. In FIG. 3 the arrow A indicates a pulling direction of the cable 738 in the sheath 729 in order to actuate the tool, closing the tool jaws.

Referring now to FIGS. 3 and 4, these views illustrate further details of the bellcrank mechanism 748. This mechanism is used to transfer the cable actuation action from the lever 722, via the transfer disc assembly 760 to the tool actuation cable 762. The bellcrank mechanism 748 includes arm 764 and yoke 768. The arm and yoke are disposed on either side of the pivot 769. The bellcrank pivot 769 is, in turn, supported from a mounting boss 752 that is fixed to the ball 715. In this way, when the proximal bendable member is pivoted such as to the position shown in FIG. 5, the support for the bellcrank mechanism moves therewith.

In FIG. 4A the bellcrank mechanism is shown in a perspective view. The yoke 768 has opposite legs that terminate at 768A and 768B. These terminating ends form pads that are adapted to be urged against the transfer disc assembly 760. A separate resilient pad may be attached at 768A, 768B.

The transfer disc assembly 760 is supported by the proximal stub shaft 753. One end of the shaft 753 is supported at or integral with the hub 701. The rotation knob 724 is fixed to the other end of the stub shaft 753 as noted in FIG. 2. A set screw 754 is illustrated in FIG. 2 for securing the rotation knob 724 to the proximal stub shaft 753. An end plate 755 also supports the stub shaft 753. FIG. 2 also illustrates bearings 756 and 757 for respectively supporting the end plate 755 and the hub 701 from the spherical ball 715. In this way, the rotation knob 724, the transfer disc assembly 760 and the entire proximal bendable member are supported for rotation relative to the spherical ball 715.

The transfer disc assembly 760 is illustrated in a separate perspective view in FIG. 4B. This assembly includes an outer disc 780 and a concentrically arranged inner disc 782. The discs 780 and 782 are interconnected by four pins 784. These pins are adapted to ride in corresponding slots 785 in the proximal stub shaft 753 to allow linear translation of the transfer disc assembly 760. Refer to FIGS. 2-4 for an illustration of the position of the slots 785 as they relate to the pins 784. This slot arrangement permits a limited amount of linear travel of the transfer disc assembly 760 in the longitudinal direction of the proximal stub shaft 753. FIG. 2 shows the transfer disc assembly 760 at the right end of the slot 785. This corresponds to an unactuated position of the tool actuation lever 722. FIG. 3, on the other hand, shows the transfer disc assembly 760 at or near the left end of the slot 785 corresponding to an actuated position of the tool actuation lever 722.

FIGS. 2 and 3 also illustrate the cable return spring 783. This is disposed, at one side at a fixed disc 787 that forms a spring seat. The disc 787 is maintained in place in the proximal stub shaft 753 by means of one or more set screws 789. The opposite end of the return spring 783 is urged against the inner disc 782 of the transfer disc assembly 760. Thus, the return spring 783 biases the transfer disc assembly 760 to the right in FIG. 3 so as to normally position the end effector in its open jaw position.

FIG. 3 illustrates the actuation cable 738 having been pulled in the direction of arrow A to move the transfer disc assembly, via the yoke 768 to an actuated position. In FIG. 3 the arrow B indicates the linear direction of movement of the transfer disc assembly 760. The inner disc 782 has a central passage for receiving the tool actuation cable 762. FIG. 3 shows the swedged cable end ball 792 that is attached to the cable 762 and that captures the cable in the transfer disc assembly 760. The movement of the transfer disc assembly 760 in the direction of arrow B, of course, moves the tool actuation cable 762 in the same direction. The tool actuation cable 762 is shown in FIGS. 2 and 3 as disposed in a cable sheath 794 that also extends through the proximal bendable member. The tool actuation cable 762 actuates the end effector in a manner similar to that described in U.S. Ser. No. 11/185,911.

The medical instrument illustrated in FIGS. 1-5 also has a locking feature. This is illustrated, for example, in FIG. 1 by the locking lever 795 that is pivotally mounted to the handle housing. The locking lever 795 actuates a friction pad 797 that is urged by the lever 795 against the outer spherical surface of the spherical ball 715. In one position of the lever 795, such as shown in FIG. 1, it is disengaged so that the ball is readily rotatable within the socket 717. In the other position of the lever 795, such as shown in FIG. 5, it is urged against the friction pad 797 which, in turn, engages the outer spherical surface of the ball 715. In this locked position the ball is prevented from any further rotation in the socket 717, thus maintaining the bendable members in a particular selected position. However, even in this locked position the tip of the instrument can still be rotated via the rotation knob 724 to change the orientation of the end effector. The rotation knob 724 and proximal bendable member 718 are rotatably supported in the handle to enable this rotation even when the instrument position is locked.

Reference is now made to FIGS. 6-10 for still a further embodiment of the present invention. This embodiment is somewhat simplified in that it does not require the use of bellows or a series of interconnecting discs, particularly at the proximal end of the instrument. In this embodiment the entire instrument is not disclosed but it is understood that the entire instrument will include a complete handle assembly and a complete distal section with an end effector. A portion of the distal bendable member is shown in FIG. 6. In this embodiment the distal bendable member is a unitary structure. In FIG. 6 the handle is more of an in-line type than a pistol grip.

FIG. 6 is a fragmentary cross-sectional plan view of the instrument of this embodiment showing only portions of the handle 812, the instrument shaft 814 and the distal bendable member 820. For further details of the distal portion of the instrument, reference may be made to U.S. Ser. No. 11/185,911 hereby incorporated herein by reference in its entirety. In FIG. 6 the cables 800 are shown extending through the instrument shaft 814 and coupled to the end effector which is not specifically illustrated in FIG. 6. The construction of the handle is only shown in a fragmentary view at the interface with the proximal bendable member 818. The handle includes a lever for actuating the tool actuation cable 838. Again, reference is made to FIGS. 1-5 herein and to U.S. Ser. No. 11/185,911 for further details of the handle mechanism and actuation lever. In the embodiment of FIGS. 6-10 the handle is preferably of straight construction.

FIG. 7 is a cross-sectional view taken in FIG. 6 along line 7-7. FIG. 8 is a cross-sectional view also taken in FIG. 6 along line 8-8. FIG. 9 is an exploded perspective view of a portion of the mechanism of the embodiment of FIG. 6. FIG. 10 is a fragmentary cross-sectional view showing an alternate embodiment for the support of the inner shaft.

In the embodiment of FIG. 6, the handle 812 is constructed in two halves including the handle halves 812A and 812B (see FIG. 9). It is the tilting of the handle 812 relative to the adaptor 826 that controls the distal bending at the distal bendable member 820. Alternatively one may consider the shaft tilting relative to the handle. The rotation knob 824 is integral with the adaptor 826 and provides for rotation of the instrument shaft, particularly rotation of the outer tube 832 of the instrument shaft relative to the inner tube 834 of the instrument shaft. The rotation of the outer tube 832 of the instrument shaft rotates the distal bendable member and the end effector that is supported at the distal end thereof. This provides for rotation at the tip of the instrument about a distal tip axis, such as the axis P in FIG. 5.

The outer shaft tube 832 is secured within the adaptor 826. The inner tube 834 is supported relative to the outer tube 832 by way of bearings 833 and 835. These bearings enable the outer tube 832 to rotate relative to the fixed position inner tube 834. The bearings 833 and 835 are preferably provided with through holes or slots for receiving the cables 800 which pass therethrough. Within the instrument shaft 814 there may also be provided spacers (not shown) with guide slots for the cables 800. In the embodiment illustrated in FIGS. 6-10, four control cables 800 are provided as shown in the cross-sectional view of FIG. 7. In other embodiments fewer or greater than four cables may be provided.

The very proximal end 836 of the inner tube 834 supports the ball 815. The ball 815 is fixedly mounted on the end of the inner shaft which does not rotate. As noted in FIG. 6, the tool actuation cable 838, which is contained in a flexible sheath 839 passes through the ball 815. For this purpose the ball 815 is provided with a somewhat conical cavity 817. In FIG. 6 the handle is shown in its tilted position and the cavity 817 permits the tool actuation cable 838 and the sheath 839 to deflect in the cavity 817 without any binding between the cable and the ball.

The ball 815 is firmly attached to the proximal end 836 of the inner tube 834 and thus may be considered as substantially nonrotatable. The tilting of the end effector in three dimensions is performed by the handle 812 having the capability of likewise being bent or tilted in three dimensions relative to the adaptor 826. For this purpose the handle 812 is provided in two halves that define therebetween the ball socket 825. Refer also to FIG. 9 that shows the handle halves 812A and 812B that are interengaged with the use of locking pins 807. The exploded view of FIG. 9 also illustrates the spherical ball 815 and the accommodating ball socket 825 in the handle 812. The ball 815 is provided with diametrically disposed pins 827 that are accommodated in diametrically disposed slots 828 in the handle at the ball socket 825. This pin and slot arrangement enables the handle to move in three dimensions relative to the ball 815. The pin 827 may transition in the slot 828 when the handle is moved in the plane of the paper in FIG. 6. Also, the handle can pivot relative to the pin 827 as the handle is moved in and out of the plane of the paper in FIG. 6. This provides three dimensional positioning.

FIG. 6 also illustrates the rotating anchor ring 840 that is supported relative to the handle 812 and that carries the very proximal end of each of the cables 800. For this purpose, the rotating anchor ring 840 includes four holes disposed at 90 degrees to each other and that receive the proximal ends (balls 841) of each of the cables 800. FIGS. 6 and 7 show the cable anchor balls 841 that are the proximal termination for each of the cables. A spring 842 is provided between each of the cable terminations and the rotating anchor ring 840. In the position illustrated in FIG. 6 it is noted that the handle is tipped upwardly. As long as the cables 800 are not twisted within the instrument shaft, then this tilting of the handle causes a corresponding downward movement of the end effector by way of the distal bendable member 820.

The proximal bendable member 818 may be also considered as including the retainer 844 and the metal reinforcing ring 846. The metal reinforcing ring 846 secures the two handle halves together and secures the socket 825 about the ball 815. The reinforcing ring 846 may be secured in place by a snap fit with or without the use of some type of a restraining device. The retainer 844 is adjacent to the metal reinforcing ring and holds the rotating anchor ring 840 in place while permitting rotation of the rotating anchor ring 840 relative to the handle 812. A raceway 847 is provided between the rotating anchor ring 840 and the handle 812.

As indicated previously, the rotating anchor ring 840 represents the means for holding the very proximal ends of the cables 800. Also, the rotating anchor ring 840 is the interface between the rotation knob 824 and the handle. For this purpose there are provided diametrically disposed pins 849 on the ring 840 that are accommodated in arcuate slots 850 in the rotation knob 824, as depicted in FIGS. 6 and 7 This pin and slot arrangement enables the rotation knob to be rotated to, in turn, rotate the outer tube of the instrument shaft and the end effector. The rotation knob 824 rotates the end effector regardless of the position of the handle and the pins 849 move in slots 850 to enable this rotational movement. As with the other pin and slot arrangement 827, 828, the pin 849 and slot 850 enable rotational motion of the rotation knob 824 regardless of the position of the handle relative to the instrument shaft.

The cross-sectional view of FIG. 6 also depicts the locking mechanism that is used with the proximal bendable member 818. This locking mechanism includes the sleeve 852 that supports a flange 853 at one end and the cup 854 at the other end. The cup 854 is arranged in a seat 855. Refer to FIG. 9 for an illustration of the seat 855 that receives the cup 854. The sleeve 852 is adapted to transition linearly toward and away from the ball 815. In one position the sleeve is disposed away from the ball and in the opposite position it is moved into contact with the ball for locking the position of the handle relative to the ball 815.

The translation of the sleeve 852 is controlled from the wedge 856. The wedge 856 has a flat surface that bears against the flange 853 and has a tapered surface that engages a tapered wall 857 of the handle. The wedge 856 also includes an elongated slot 858 that provides sufficient clearance so that, as the wedge member 856 is moved between its locked and unlocked positions, there is no contact with the tool actuation cable and its associated sheath. The cross-sectional view of FIG. 8 illustrates the wedge member 856 and its associated elongated slot 858.

The wedge member 856 is controlled by means of a pair of buttons. This includes a lock button 860 supported at the end of shaft 861. Shaft 861 is fixed to the wedge member 856. On the opposite side of the wedge member 856, as depicted in FIG. 6, there is a release button 862 that is supported from the wedge member by means of the shaft 863. Refer also to the cross-sectional view of FIG. 8.

When the lock button 860 is pushed inward toward the handle this causes the wedge member 856 to move against the tapered surface 857 thus moving the sleeve 852 longitudinally so that the cup 854 applies a clamping pressure or force on the ball 815. When this occurs the handle 812 is held in a fixed position relative to the ball 815. In other words whatever position the instrument is in at the time that the button 862 is depressed, the instrument is maintained in that position with the end effector at the particular corresponding position.

The locking member may be released by pushing on the release button 862 so as to move the wedge member 856 longitudinally in the opposite direction. This releases the tension on the sleeve 852 so that it is no longer in intimate contact with the ball 815. This enables the handle to be moved in any three dimensional position relative to the adaptor 826. Biasing means or detent means may be associated with the locking mechanism.

Reference is now made to the fragmentary cross-sectional view of FIG. 10. FIG. 10 is a schematic illustration of an alternate embodiment in which the ball 815 is rotationally mounted on the end of the inner shaft 834. This rotational mounting is carried out by means of the bearing 808 illustrated in FIG. 10. In this particular embodiment the bearings 833 and 835 illustrated in FIG. 6 are not used and the inner and outer tubes 832 and 834 thus rotate together.

Figure 11:
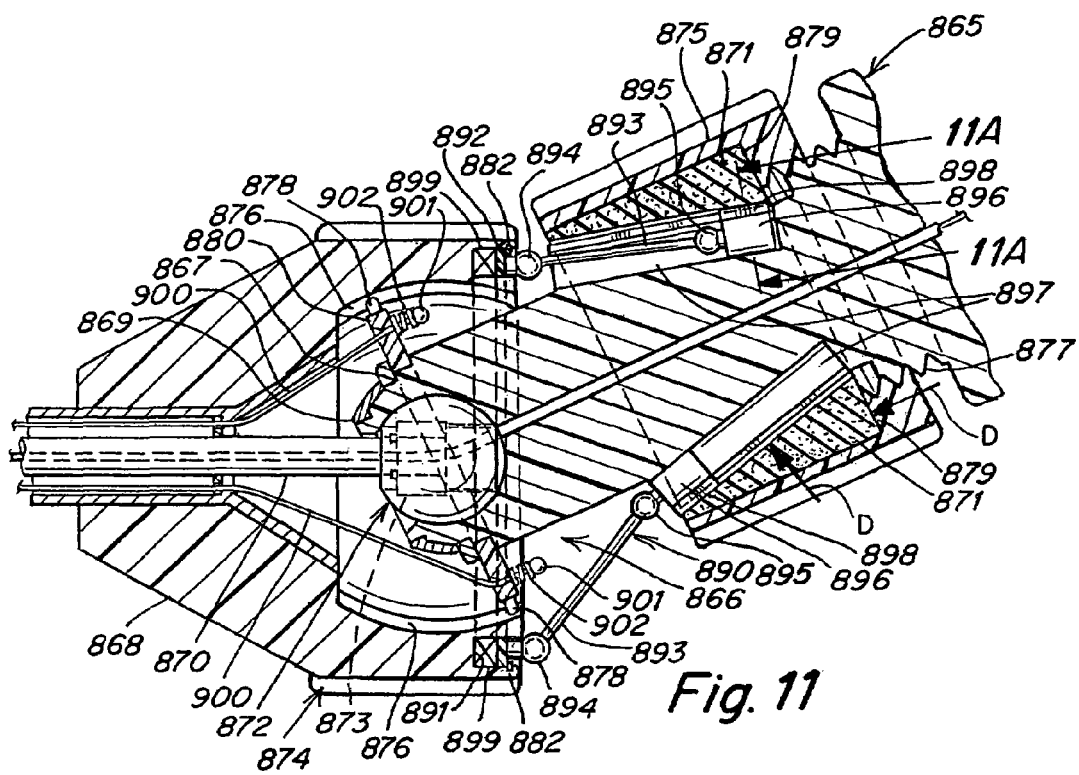
FIG. 11 is a fragmentary cross-sectional side view of still another embodiment of the instrument.
Figure 11A:
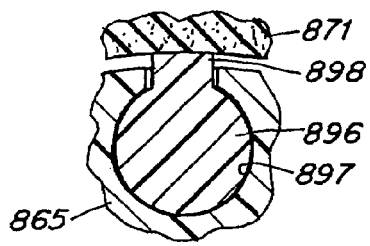
FIG. 11A is a fragmentary cross-sectional view taken along line 11A-11A of FIG. 11.
Figure 12:
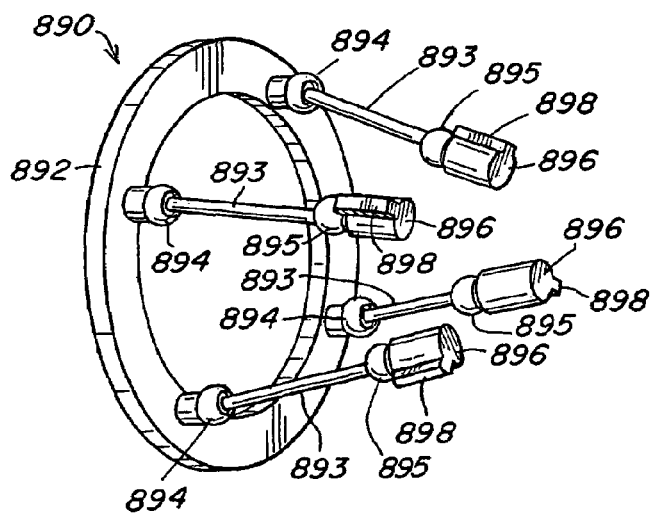
FIG. 12 is a schematic perspective view of the bearing ring and piston assembly of FIG. 11.

Still another embodiment of the present invention is illustrated in FIGS. 11, 11A and 12. In this embodiment the entire instrument is not shown. It is understood that the handle 865 includes a mechanism for actuating the tool actuation cable. At the distal end of the instrument there is an instrument shaft coupling by way of a distal bendable member to an end effector. In this embodiment the illustration is primarily of the proximal bendable member 866. The proximal bendable member 866 includes a ball joint that further employs sliding rods or pistons that are clamped to hold and lock the instrument in a desired position. This rod and piston arrangement functions as a follower relative to the bending action.

FIG. 11 is a fragmentary cross-sectional side view of this embodiment of the invention. FIG. 11A is a fragmentary cross-sectional view taken along line 11A-11A of FIG. 11. FIG. 12 is a schematic perspective view of the bearing ring and piston assembly used in the embodiment of FIG. 11.

In the fragmentary cross-sectional view of FIG. 11 the handle 865 interfaces with the adaptor 868. The adaptor 868 may be substantially similar to the adaptor 826 illustrated in the embodiment of FIG. 6. Likewise, the instrument depicted in FIG. 11 includes an outer shaft tube that is not illustrated in FIG. 11 but that may be the same as that illustrated in FIG. 6. FIG. 11 does illustrate the inner tube shaft 870 that connects to the ball 872. That connection may be substantially the same as that illustrated in FIG. 10 with the use of a bearing 873 so that the inner and outer tubes of the instrument shaft rotate together.

The adaptor 868 has formed integral therewith, the rotation knob 874 that may be of a configuration almost the same as that shown in the cross-sectional view of FIG. 7. The adaptor 868 is also provided with a slot or track 876, one at separate diametrically disposed positions as illustrated in FIG. 11. This track 876 receives a respective pin 878 of the anchor ring 880. The adaptor 868 also receives the bearing ring and piston assembly 890 that is illustrated in a schematic perspective view in FIG. 12. For this purpose there is provided an annular slot in the adaptor at its proximal side that forms the raceway 891 for the bearing 899. A snap ring 882 holds the assembly 890 in place at the adaptor. In the embodiment of FIG. 11 the piston assembly 890 functions as a follower as the handle is manipulated to move the pistons in and out.

The bearing ring and piston assembly 890 is illustrated in a perspective view in FIG. 12 and includes the ring 892 and a plurality of rods 893 that are arranged at 90 degree intervals about the ring 892. A joint is formed at each end of each rod. Each of these joints is depicted in FIG. 12 as a ball and socket joint. However, it is understood that other types of limited pivot joints may also be used such as a hinge joint or living hinge. Thus, each rod has at respective ends the joints 894 and 895. These joints provide at least limited pivoting of each rod relative to the ring 892. FIG. 11 depicts the positioning of the rods relative to the ring 892 in a bent condition of the proximal bendable member 866.

The joints 894 connect the rods to the ring 892 while the joints 895 connect the opposite end of the rods to respective pistons 896. Each of the pistons 896 are accommodated in open cylinders 897 in the handle 865. FIG. 11 illustrates a top piston 896 at one end of the cylinder 897 and a lower piston 896 at an opposite end of that cylinder. Each piston 896 has an elongated rib 898 that extends through a slot in the housing so that it can be contacted by the resilient member 871. The resilient member 871 is preferably annular in shape and is held in position by means of the locking knob 875. The resilient member 871 has a tapered surface that is adapted to contact the piston rib 898 to hold the pistons in the selected position thus maintaining the proximal and distal bendable members in their selected position.

The annular locking knob 875 captures the resilient member 871 and includes a threaded engagement with the handle 865. This is shown in FIG. 11 at 877. The rotation of the locking knob 875 causes the contact surfaces at 879 between the knob 875 and resilient member 871 to engage and force the resilient member against the piston rib 898 to lock the position. FIG. 11 illustrates by arrows D the direction of transition of the locking knob 875 and of the resilient member 871.

FIG. 11 also illustrates the rotating anchor ring 880 that is supported relative to the handle 865 and that carries the very proximal end of each of the cables 900. For this purpose, the rotating anchor ring 880 includes four holes disposed at 90 degrees to each other and that receive the proximal ends of each of the cables 900. FIG. 11 shows the cable anchor balls 901 that are the proximal termination for each of the cables. A spring 902 is provided between each of the cable terminations and the rotating anchor ring 880. In the position illustrated in FIG. 11 it is noted that the proximal bendable member is tipped relative to the handle 865. Depending upon whether the cables 800 are twisted or not within the instrument shaft, then this relative tilting between the handle and proximal bendable member causes a corresponding downward or upward movement of the end effector by way of the distal bendable member.

The proximal bendable member 866 may be also considered as including the retainer 867 and the metal reinforcing ring 869. The metal reinforcing ring 869 secures the two handle halves together and secures the handle socket about the ball 872. The reinforcing ring 869 may be secured in place by a snap fit with or without the use of some type of a restraining device. The retainer 867 is disposed adjacent to the metal reinforcing ring and holds the rotating anchor ring 880 in place while permitting rotation of the rotating anchor ring 880 relative to the extension of the handle 865. As noted previously, a raceway is provided between the rotating anchor ring 880 and the handle 865.

As indicated previously, the rotating anchor ring 880 represents the means for holding the very proximal ends of the cables 900. Also, the rotating anchor ring 880 is the interface between the rotation knob 874 and the handle 865. For this purpose there are provided diametrically disposed pins 878 that are accommodated in arcuate slots or tracks 876 in the rotation knob 874. This pin and slot arrangement enables the rotation knob to be rotated to, in turn, rotate both the inner and the outer tube of the instrument shaft and the end effector. The rotation knob 874 rotates the end effector regardless of the position of the handle and the pins 878 move in slots 876 to enable this rotational movement.

In the embodiment of FIGS. 11-12 it is noted that the anchor ring 880 is attached to the handle but is rotatable relative thereto. It is the relative movement (tilting) between the proximal bendable member and the handle, in three dimensions, which controls the positioning of the distal bendable member via the cables 900. Once the surgeon has the instrument in a desired position and wishes to lock the instrument in that particular position, then the locking ring or knob 875 is screwed in the direction of arrow D in FIG. 11. The threads 877 are preferably coarse so that the knob 875 does not have to be rotated to any great extent in order to lock the instrument position. This rotation of the knob 875 pushes on the resilient member 871 which, in turn, moves that member into engagement with piston ribs or slides 898. This same action occurs at each of the pistons 896 thus firmly locking the position of the proximal bendable member and, in turn, the position of the distal bendable member. The locking action is released by rotating the knob 875 in the opposite direction. Either left or right hand threads 877 may be used.

Figure 13:
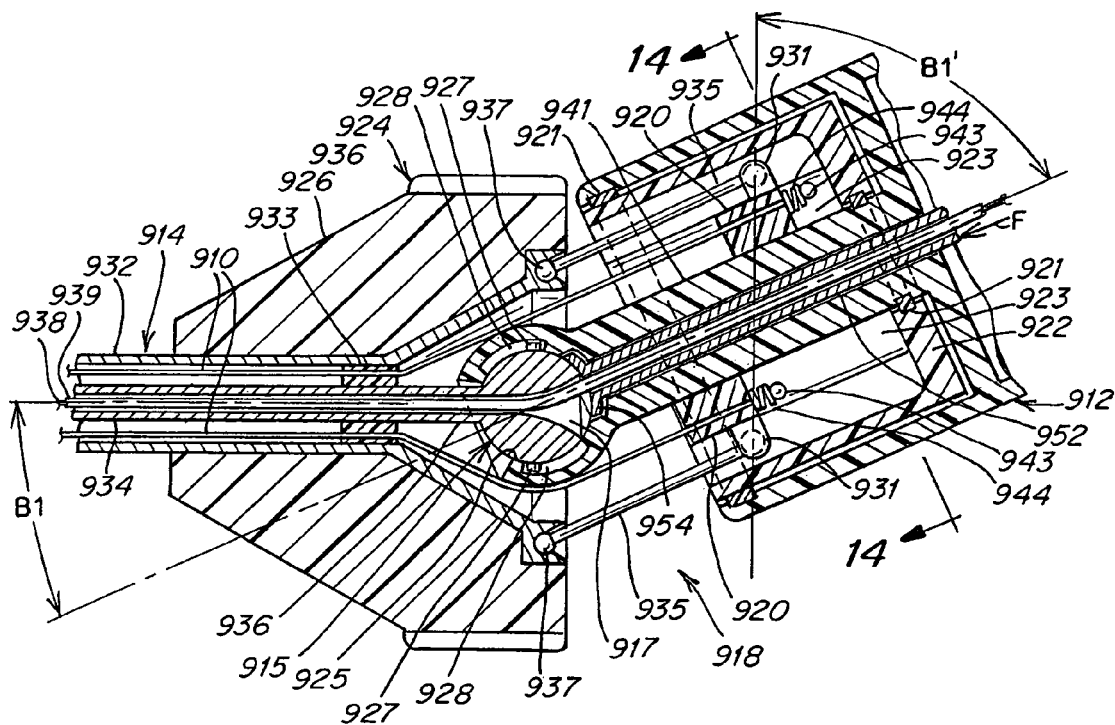
FIG. 13 is a cross-sectional side view of still a further embodiment of the present invention.
Figure 14:
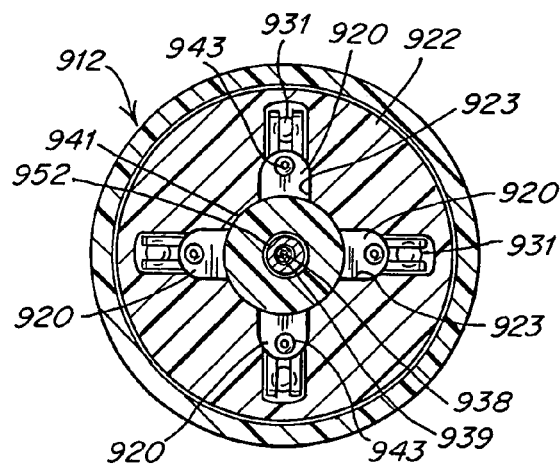
FIG. 14 is a cross-sectional end view taken along line 14-14 of FIG. 13.

Still a further embodiment of the present invention is illustrated in FIGS. 13 and 14. In this embodiment the entire instrument is not shown. It is understood that the handle 912 includes a mechanism for actuating the tool actuation cable such as the lever arrangement of FIG. 1. At the distal end of the instrument there is an instrument shaft coupling by way of a distal bendable member to an end effector. In this embodiment the illustration is primarily of the proximal bendable member 918. The proximal bendable member 918 includes a ball and socket arrangement that further employs sliding and pivoting rods or pistons, in combination with a locking mechanism similar to that shown previously in FIG. 6.

FIG. 13 is a cross-sectional side view of still a further embodiment of the present invention similar to the embodiment of FIG. 11 in that it employs limited pivoting rods or pistons. FIG. 14 is a cross-sectional end view taken along line 14-14 of FIG. 13.

In the embodiment of FIG. 13, the handle 912 may be constructed in two halves and is preferably of straight construction but may also be of a pistol grip type. It is the tilting of the handle 912 relative to the adaptor 926 that controls the distal bending at the distal bendable member which is not shown in FIG. 13, but may be of the type previously described. The rotation knob 924 is integral with the adaptor 926 and provides for rotation of the instrument shaft 914, particularly rotation of the outer tube 932 of the instrument shaft relative to the inner tube 934 of the instrument shaft. The rotation of the outer tube 932 of the instrument shaft rotates the distal bendable member and the end effector that is supported at the distal end thereof. This provides rotation of the tool about its distal tool axis.

The outer shaft tube 932 is secured within the adaptor 926. The inner tube 934 is supported relative to the outer tube 932 by way of bearings at each end of the instrument shaft 914. In FIG. 13 only one bearing 933 is illustrated, it being understood that a bearing is also provided at the distal end of the instrument shaft, as in FIG. 6. These bearings enable the outer tube 932 to rotate relative to the fixed position inner tube 934. The shaft support bearings are preferably provided with through holes or slots for receiving the cables 910 which pass therethrough. Within the instrument shaft 914 there may also be provided spacers (not shown) with guide slots for the cables 910. In the embodiment illustrated in FIGS. 13 and 14, four control cables 910 may be provided as shown in the cross-sectional view of FIG. 14. In other embodiments fewer or greater than four cables may be provided.

In the embodiment illustrated in FIG. 13 the outer tube 932 is rotatable relative to the inner tube 934. For this purpose bearings are provided between the inner and outer tubes. In an alternate embodiment the inner and outer portions of the instrument shaft may rotate together in which case the bearing is between the inner tube and ball, as in the illustration of FIG. 10.

The very proximal end 936 of the inner tube 934 supports the ball 915. The ball 915 is fixedly mounted on the end of the inner shaft which does not rotate. As noted in FIG. 13, the tool actuation cable 938, which is contained in a flexible sheath 939 passes through the ball 915. For this purpose the ball 915 is provided with a somewhat conical cavity 917. In FIG. 13 the handle is shown in its tilted position and the cavity 917 permits the tool actuation cable 938 and the sheath 939 to deflect in the cavity 917 without any binding between the cable and the ball.

The ball 915 is firmly attached to the proximal end of the inner tube 934 of the instrument shaft and thus may be considered as substantially nonrotatable. The tilting of the end effector in three dimensions is performed by the handle 912 having the capability of likewise being bent or tilted in three dimensions. For this purpose the handle 912 may be provided in two halves that define therebetween the ball socket 925. The handle halves may be interlocked with the use of aligned locking pins. The socket 925 is disposed at the terminal end of the handle collar 941. The ball 915 is provided with diametrically disposed pins 927 that are accommodated in diametrically disposed slots 928 in the handle at the ball socket 925. This pin and slot arrangement enables the handle to move in three dimensions relative to the ball 915. The pin 927 may transition in the slot 928 when the handle is moved in the plane of the paper in FIG. 13. Also, the handle can pivot relative to the pin 927 as the handle is moved in and out of the plane of the paper in FIG. 13.

The cross-sectional view of FIG. 13 also depicts part of the locking mechanism that is used with the proximal bendable member 918. This mechanism may be like the one shown and previously described in connection with the embodiment of FIG. 6. This locking mechanism includes the sleeve 952 that supports a flange (not shown in FIG. 13) at one end and the cup 954 at the other end. The cup 954 is arranged in a seat of the socket 925. The sleeve 952 is adapted to transition linearly toward and away from the ball 915. In one position the sleeve is disposed away from the ball and in the opposite position it is moved into contact with the ball for locking the position of the handle relative to the ball 915. The translation of the sleeve 952 is controlled from a wedge arrangement such as illustrated in FIG. 6. Movement of the sleeve 952 in the direction of arrow F in FIG. 13 locks the cupped end 954 against the ball 915 thus holding the proximal bendable member in the desired selected locked position.

In the embodiment shown in FIG. 13, rather than using an anchor ring for retaining the ends of the cables 910, each of the cables 910 is held by a slider 920. Each of the sliders 920 is, in turn, held by the rotatable cage 922 in a corresponding slider channel 923. FIG. 13 illustrates the bearings 921 that support the cage 922 relative to the handle 912. The cage 922 is supported to rotate in response to rotation of the rotation knob 924 via the links 935. Each of the sliders 920 is slideable in its respective channel 923. Each slider 920 retains the end of a respective control cable 910. For this purpose each cable is provided with an end anchor lug 943 held by the slider 920. A spring 944 is also illustrated for biasing the cable 910. FIG. 13 illustrates the top cable 910 being pulled while the corresponding bottom cable is relaxed.

The links 935 form a transmission means between the adaptor 926 and the instrument handle 912. Limited motion joints are provided at the respective ends of these links 935. Thus, each link 935 has one joint 937 that enables the link to have some limited pivoting relative to the adaptor 926. The other end of the link supports another joint 931 that likewise allows some limited pivoting of the link relative to the slider 920.

FIG. 13 shows the instrument with the handle bent at an angle to the longitudinal center axis of the instrument shaft. This is illustrated in FIG. 13 as at an angle B1. The complement to that angle is also shown in FIG. 13 as angle B1' which is between the longitudinal axis of the handle and a line through the joints 931.

Figure 15:
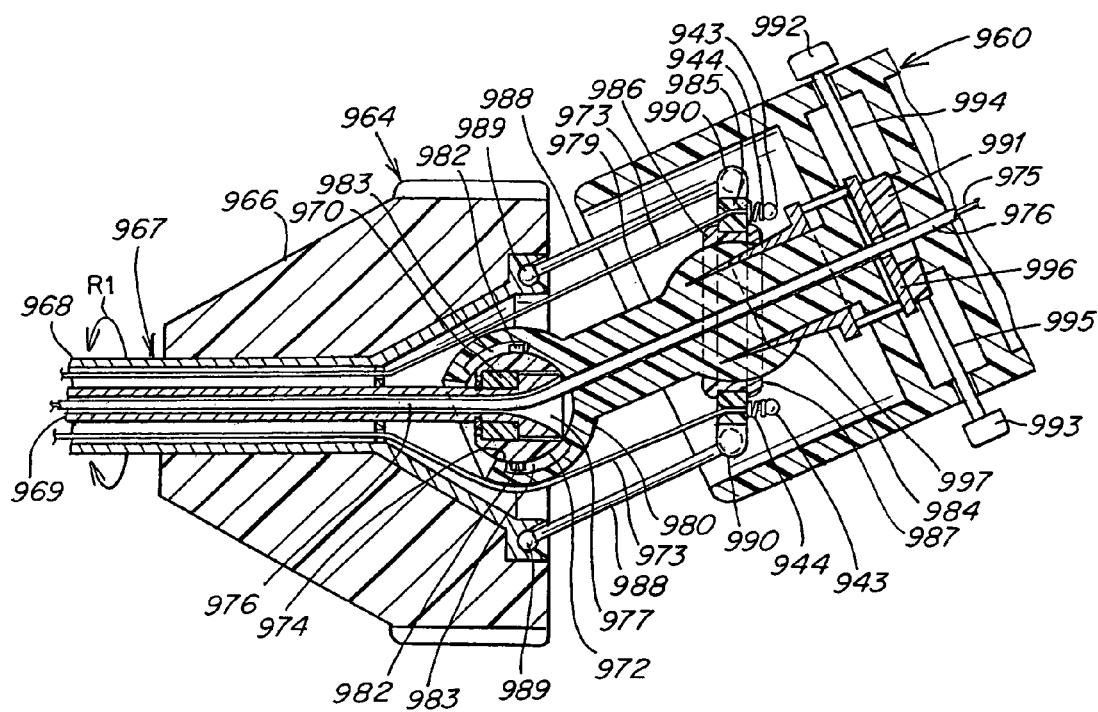
FIG. 15 is a cross-sectional side view of still another embodiment of the instrument of the present invention.

FIG. 15 is a cross-sectional side view of still a further embodiment of the present invention similar to the embodiment of FIG. 13 in that it employs motion rods or links for controlling the cabling.

In the embodiment of FIG. 15, the handle 960 may be constructed in two halves and may be of straight construction or of a pistol grip type. It is the tilting of the handle 960 relative to the adaptor 966 that controls the distal bending at the distal bendable member which is not shown in FIG. 15, but may be of the type previously described. The rotation knob 964 is integral with the adaptor 966 and provides for rotation of the instrument shaft 967, particularly rotation of the outer tube 968 of the instrument shaft, along with the inner tube 969 of the instrument shaft. The rotation of the inner and outer tubes of the instrument shaft rotates the distal bendable member and the end effector that is supported at the distal end thereof. FIG. 15 illustrates the shaft rotation by the arrow R1.

The outer shaft tube 968 is secured within the adaptor 966. The inner tube 969 is supported relative to the outer tube 968 so as to rotate together like the embodiment shown in FIG. 10. This embodiment includes a bearing 970 that enables relative rotation between the inner shaft tube 989 and the ball 972. In the embodiment illustrated in FIG. 15, four control cables 973 may be provided to provide three dimensional positioning. In other embodiments fewer or greater than four cables may be provided.

In the embodiment illustrated in FIG. 13 the outer tube 932 is rotatable relative to the inner tube 934. For this purpose bearings are provided between the inner and outer tubes. However, in the embodiment of FIG. 15 the inner and outer portions of the instrument shaft rotate together in which case the bearing is between the inner tube and ball, as in the illustration of FIGS. 10 and 15.

The very proximal end of the inner tube 969 supports the ball 972 via the bearing 970. The ball 972 is positioned in the handle socket 974. As noted in FIG. 15, the tool actuation cable 975, which is contained in a flexible sheath 976, passes through the ball 972. For this purpose the ball 972 is provided with a somewhat conical cavity 977. In FIG. 15 the handle is shown in a tilted position relative to the proximal bendable member, and the cavity 977 permits the tool actuation cable 975 and the sheath 976 to deflect in the cavity 977 without any binding between the cable and the ball.

The ball 972 is rotatably attached to the proximal end of the inner tube 969 of the instrument shaft and is rotatable in the handle socket 974. The tilting of the end effector in three dimensions is performed by the handle 960 having the capability of likewise being bent or tilted in three dimensions. For this purpose the handle 960 may be provided in two halves and further includes handle tube 979 that has, at its distal end, the cupped end 980 at which is defined the ball socket 974. The handle halves may be interlocked with the use of aligned locking pins. The ball 972 is provided with diametrically disposed pins 982 that are accommodated in diametrically disposed slots 983 in the handle at the ball socket 974. This pin and slot arrangement enables the handle to move in three dimensions relative to the ball 972. The pin 982 may transition in the slot 983 when the handle is moved in the plane of the paper in FIG. 15. Also, the handle can pivot relative to the pin 982 as the handle is moved in and out of the plane of the paper in FIG. 15.

The embodiment of FIG. 15 also illustrates a sphere 984 that is formed along the tube 979. The sphere 984 supports the anchor ring 985 by way of the rider 986. A retainer 987 holds the anchor ring 985 in place. A raceway is formed between the anchor ring 985 and rider 986.

The links or pins 988 form a transmission means between the adaptor 966 and the instrument handle 960, and more particularly the anchor ring 985. Limited motion joints are provided at the respective ends of these links 988. Thus, each link 988 has one joint 989 that enables the link to have some limited pivoting relative to the adaptor 966. The other end of the link supports another joint 990 that likewise allows some limited pivoting of the link relative to the anchor ring 985.

The cross-sectional view of FIG. 15 also depicts the locking mechanism that is used with the proximal bendable member. This mechanism is similar to the one shown and previously described in connection with the embodiment of FIG. 6. This locking mechanism includes a slide button arrangement that controls the wedge member 991. The wedge member 991 is controlled by means of a pair of buttons. This includes a lock button 992 supported at the end of shaft 994. Shaft 994 is fixed to the wedge member 991. On the opposite side of the wedge member 991, as depicted in FIG. 15, there is a release button 993 that is supported from the wedge member by means of the shaft 995.

When the lock button 992 is pushed inward toward the handle this causes the wedge member 991 to move against the surface of slide piece 996 thus moving the cone 997 into the split in the ball 984. When this occurs the handle 960 is held in a fixed position relative to the proximal bendable member and rotation knob. In other words whatever position the instrument is in at the time that the button 992 is depressed, the instrument is maintained in that position with the end effector at a desired location. The movement of the cone 997 into the ball causes the outer surface of the ball to lock against the rider 986.

The locking member may be released by pushing on the release button 993 so as to move the wedge member 991 in the opposite direction. This releases the tension on the cone so that it is no longer in intimate contact with the ball 984. This enables the handle to be moved in any three dimensional position relative to the adaptor 966.

Having now described a limited number of embodiments of the present invention it should now be apparent to those skilled in the art that other embodiments and modifications thereof are contemplated a falling within the scope of the present invention. For example, the embodiments described herein have primarily used four control cables for providing all direction motion of the motion members. In alternate embodiments fewer or greater numbers of cables may be provided. In a most simplified version only two cables are used to provide single DOF action at the bendable motion member. Another example is that existing alternate embodiments show either a pistol grip or an in-line handle structure, but it is understood that all embodiments can use either type of handle structure. In the illustrated embodiments a rotation knob has been used to perform the function of rotating the distal instrument tip. In an alternate embodiment of the invention other means may be provided to accomplish such tip rotation. For example, a slide member may be used in place of a rotation knob, or any other moveable member that controls the instrument shaft and instrument tip for rotation of the end effector about a distal tool axis such as shown in FIG. 1 (axis P). Also, in, for example, the embodiment of FIGS. 1-5, the rotation knob 724 provides both the rotation feature (for control of the tool about axis P), as well as the pivotal control of the bending action. In an alternate embodiment of the present invention the knob 724 can be used only for controlling bending or tilting, with the rotation controlled separately by a knob, such as the knob 721 shown in FIG. 1. The knob 724 may also be replaced by a lever arrangement to control bending.

What is claimed is:

1. A medical instrument comprising:
   a proximal control handle;
   a distal work member;
   a proximal movable member controlled from said proximal control handle;
   a distal movable member controlled from said proximal movable member to provide controlled movement of said distal work member via said proximal and distal movable members;
   an instrument shaft that intercouples said proximal and distal movable members;
   and actuation means coupled between said movable members;
   a ball and socket assembly that includes a ball member pivotally retained by a socket defined in said proximal control handle and constructed and arranged for three dimensional motion relative to the socket;
   said proximal movable member controlled by the ball member for three dimensional motion therewith;
   said movable members both comprising bendable members and further including a rotation knob coupled to at least one of the proximal bendable member and the instrument shaft;
   said rotation knob controlling the rotation of the proximal bendable member and, in turn, the instrument shaft, distal bendable member and distal work member;
   wherein the internal cavity of the ball member comprises a conical cavity that provides a conical space in which the proximal bendable member is pivotable to enable the three dimensional motion.

2. The medical instrument of claim 1 further including a locking member supported from said proximal control handle and having locked and unlocked states; said locking member in said unlocked state enabling control of said distal work member from said proximal bendable member; and said locking member, in said locked state, holding said bendable members in a desired fixed position.

3. The medical instrument of claim 2 wherein said locking member, in the locked state, fixes the position of the proximal bendable member by locking the ball member in the socket.

4. The medical instrument of claim 1 wherein both said distal and proximal bendable members comprise a uni-body structure forming respective distal and proximal bendable members.

5. The medical instrument of claim 1 including first bearing means for rotatably supporting a proximal end of the proximal bendable member relative to the ball member.

6. The medical instrument of claim 5 including second bearing means for rotatably supporting the instrument shaft relative to the proximal control handle.

7. The medical instrument of claim 5 wherein said rotation knob is secured to the proximal bendable member with the first bearing means disposed therebetween.

8. The medical instrument of claim 6 wherein said rotation knob is secured to said instrument shaft distally of the second bearing means.

9. The medical instrument of claim 1 wherein a said proximal bendable member has a distal end connected to the instrument shaft and a proximal end rotatably and pivotally supported by the ball member.

10. The medical instrument of claim 9 including an actuation lever for controlling the distal work member mounted at the proximal control handle and an actuation cable controlled from the actuation lever and extending through at least the instrument shaft and bendable members.

11. The medical instrument of claim 10 including a bell crank mechanism that couples between the actuation lever and the actuation cable, responsive to operation of the actuation lever to control the actuation cable.

12. The medical instrument of claim 1 including a locking member and wherein the rotation knob and proximal bendable member are rotatably supported in the proximal control handle to enable rotation even when the instrument position is locked.

13. The medical instrument of claim 1 wherein said actuation means comprises a set of cables that couple between said bendable members, said cables terminate at one end at the proximal end of the proximal bendable member.

14. The medical instrument of claim 1 wherein said handle comprises a pistol grip handle that includes a base and a top section in which is defined the socket, said socket being a spherical socket that supports the ball member, said ball member supporting the proximal end of the proximal bendable member.

15. The medical instrument of claim 1 wherein said rotation knob is controlled for rotating the proximal bendable member and, in turn, the instrument shaft, distal bendable member and distal work member and for controlling the pivoting of the ball member in the socket.

16. A medical instrument having a proximal control handle and a distal tool that are intercoupled by an elongated instrument shaft that is meant to pass internally of an anatomic body, proximal and distal bendable members that respectively intercouple said proximal control handle and said distal tool with said instrument shaft, cable actuation means extending through the proximal and distal bendable members for coupling motion of the proximal bendable member to the distal bendable member, and a pivot ball, said control handle comprising a base and a top section that defines an at least partially spherical socket that supports the pivot ball for three dimensional pivoting therein, said proximal bendable member constructed and arranged for mounting in the pivot ball, said pivot ball being supported relative to the socket for three dimensional pivoting in the socket.

17. The medical instrument of claim 16 including a control element connected to the pivot ball for manipulating the pivot ball in the socket.

18. The medical instrument of claim 17 wherein the control element comprises a rotation knob supported in line with said proximal bendable member for controlling the three dimensional pivoting.

19. The medical instrument of claim 18 wherein said rotation knob controls the three dimensional pivoting, as well as a rotation relative to the pivot ball about a longitudinal axis of said proximal bendable member so as to control the rotation of said distal tool about a distal tool axis.

20. The medical instrument of claim 17 further including bearing means for rotatably supporting the control element in the pivot ball, a proximal end of said proximal bendable member rotatably supported in a cavity of the pivot ball.

21. The medical instrument of claim 20 wherein said bearing means has the control element connected thereto and the proximal end of the proximal bendable member is supported opposite to the control element from the bearing means.

22. The medical instrument of claim 17 including a locking means that is manually operable by a user and that locks the ball in the socket.

23. In a medical instrument having a proximal control handle and a distal tool that are intercoupled by an elongated instrument shaft that is meant to pass internally of an anatomic body, proximal and distal bendable members that respectively intercouple said proximal control handle and said distal tool with said instrument shaft, and cable actuation means extending through the proximal and distal bendable members for coupling motion of the proximal bendable member to the distal bendable member, a method of controlling the tool from the handle by means of a control element comprising; pivoting the control element in three dimensions to control the positioning of the tool in three dimensions, rotating the control element to control the rotational orientation of the tool by rotating the instrument shaft and mounting the proximal bendable member at least partially in a ball that is supported for three dimensional pivoting by means of the control element in a socket in the control handle.

24. The method of claim 23 including having the control element, not only pivot the ball in the socket, but also rotate the ball and, in turn, the instrument shaft, distal bendable member and distal tool about a longitudinal distal tool axis.

25. The method of claim 23 including constructing the control element as a single control knob that is attached to the ball.

26. The method of claim 23 including connecting the control element to the instrument shaft for rotating the instrument shaft and, in turn, the distal bendable member and tool.

27. The method of claim 25 including connecting the control element to the proximal bendable member for rotating the instrument shaft and, in turn, the distal bendable member and tool.

28. The method of claim 25 wherein the step of pivoting the control element in three dimensions includes pivoting a proximal end of the proximal bendable member in three dimensions.

29. The method of claim 28 including mounting a proximal end of the proximal bendable member in the ball so that the control element pivots the ball in the socket to bend the proximal bendable member while enabling a rotation of the proximal bendable member relative to the ball to, in turn, rotate the instrument shaft about a longitudinal axis thereof.

30. The method of claim 26 including using the control element as a rotation knob with the dual purpose of being able to firstly rotate the rotation knob to, in turn, rotate the instrument shaft and tool and to secondly pivot the rotation knob to enable the three dimensional positioning.

31. The method of claim 26 including using the control element as a rotation knob attached to the instrument shaft for the purpose of rotating the instrument shaft and, in turn, the distal bendable member and tool.

32. The method of claim 24 wherein the step of rotating the control element includes rotating the instrument shaft relative to the control handle to, in turn, rotate the distal bendable member to, in turn, rotate the tool about the longitudinal distal tool axis [P].

33. The method of claim 23 including locking the ball to the socket.

34. In a medical instrument having a proximal control handle and a distal tool that are intercoupled by an elongated instrument shaft that is meant to pass internally of an anatomic body, proximal and distal bendable members that respectively intercouple said proximal control handle and said distal tool with said instrument shaft, and cable actuation means extending through the proximal and distal bendable members for coupling motion of the proximal bendable member to the distal bendable member, a method of controlling the tool from the handle by means of a control element comprising; pivoting the control element in three dimensions to control the positioning of the tool in three dimensions, rotating the control element to control the rotational orientation of the tool by rotating the instrument shaft, constructing the control element as a single control knob, wherein the step of pivoting the control element in three dimensions includes pivoting a proximal end of the proximal bendable member in three dimensions, mounting the proximal end of the proximal bendable member in a rotation ball that is supported for three dimensional pivoting in a socket in the control handle and rotatably supporting the proximal bendable member in the ball.

35. The method of claim 34 including rotatably supporting the instrument shaft in the control handle.

36. A surgical instrument comprising:
an elongated instrument shaft having proximal and distal ends;
a tool disposed from the distal end of the instrument shaft;
a control handle disposed at the proximal end of the instrument shaft;
a distal bendable member for coupling the distal end of the elongated instrument shaft to the tool and including proximal and distal ends;
a proximal bendable member for coupling the proximal end of the elongated instrument shaft with the handle and including proximal and distal ends;
and actuation means extending between said distal and proximal bendable members so that any bending of the proximal bendable member causes a corresponding bending of the distal bendable member for controlling the positioning of the tool;
said control handle including first means for rotatably supporting the instrument shaft relative to the control handle and second means for pivotally supporting the proximal end of the proximal bendable member relative to the control handle and in three dimensions;
said second means comprising a ball member mounted in an at least partially spherical socket defined in the control handle;
said ball member defining a conical cavity that provides a conical space in which the proximal bendable member is pivotable to enable the three dimensional motion.

37. The surgical instrument of claim 36 wherein at least one of said bendable members comprise a single unitary slotted structure that is readily capable of bending in any direction and wherein said slotted structure is comprised of a plurality of separately disposed noncontiguous slots.

38. The surgical instrument of claim 36 wherein the first means comprises first bearing means supported at a flange of the control handle and rotatably engaging the instrument shaft.

39. The surgical instrument of claim 38 wherein the second means comprises second bearing means for rotatably supporting the proximal bendable member in the ball member.

40. The surgical instrument of claim 39 including a control element connected to the second bearing means and for controlling the pivoting of the ball member in the socket.

41. The surgical instrument of claim 40 wherein the proximal end of the proximal bendable member is supported at the second bearing means so as to be rotatably with both the second bearing means and control element.

42. The surgical instrument of claim 41 including an actuator cable at the control handle and a tool actuation assembly at the second bearing means for controlling the actuator cable.

43. The surgical instrument of claim 36 wherein a proximal end of the proximal bendable member is supported in the ball member with the distal end of the proximal bendable member extending into the conical cavity.

44. The surgical instrument of claim 43 including a rotation knob rotatably attached to the ball member to control the positioning of the ball member and, in turn, the proximal bendable member.

45. The surgical instrument of claim 43 including a rotation knob attached to the instrument shaft for enabling rotation thereof.

46. The surgical instrument of claim 36 including rotation means adjacent the control handle for rotating the instrument shaft.

47. The surgical instrument of claim 46 wherein the rotation means comprises a rotation knob with the dual purpose of being able to firstly rotate the rotation knob to, in turn, rotate the instrument shaft and tool and to secondly pivot the rotation knob in three dimensions to enable the three dimensional positioning of the tool.

48. The surgical instrument of claim 36 including an actuation lever for controlling the tool mounted at the control handle and an actuation cable controlled from the actuation lever and extending through at least the instrument shaft and bendable members.

49. The surgical instrument of claim 48 including a bell crank mechanism that couples between the actuation lever and the actuation cable, responsive to operation of the actuation lever to control the actuation cable and, in turn, the tool.

50. The surgical instrument of claim 36 including a lock means for fixing the position of the proximal bendable member relative to the control handle.

51. The surgical instrument of claim 50 including a bearing means for supporting the proximal bendable member in the socket in the control handle.

52. The surgical instrument of claim 51 wherein the lock means comprises a locking lever mounted in the control handle and for selective engagement with the ball member.

53. A surgical instrument comprising:
a control handle;
an instrument shaft that extends from the control handle;
a tool disposed from the distal end of the instrument shaft and controlled from the handle as to actuation and positioning thereof;
said control handle having a first section for supporting an actuation element for controlling the actuation of the tool, and a second section for supporting a positioning element for controlling the positioning of the tool;
a distal bendable member for coupling the distal end of the instrument shaft to the tool;
a proximal bendable member for coupling the proximal end of the instrument shaft to the control handle;
cable actuation means extending through the proximal and distal bendable members for coupling motion of the proximal bendable member to the distal bendable members;
said actuation element including actuation means extending at least between the distal and proximal bendable members for controlling the actuation of the tool;
said positioning element including a manually manipulated control element that is both pivotal in three dimensions to control the positioning of the tool in three dimensions and rotatable to control the rotational orientation of the tool by rotating the instrument shaft;

and means for mounting a proximal end of the proximal bendable member in a rotation ball that is supported for three dimensional pivoting in a socket in the control handle.

54. The surgical instrument of claim 53 wherein said means for mounting includes bearing means.

55. The surgical instrument of claim 53 wherein the positioning element comprises a first control knob extending from the control handle and capable of both rotation about an axis and pivoting relative to the control handle in three dimensions.

56. The surgical instrument of claim 55 including a second control knob and means for connecting the second control knob to the instrument shaft for rotating the instrument shaft and, in turn, the tool.

57. The surgical instrument of claim 53 including means for locking the ball to the socket to hold the position of the tool.

58. The surgical instrument of claim 53 including means for rotatably supporting the proximal bendable member in the ball.

59. The surgical instrument of claim 58 including bearing means for rotatably supporting the instrument shaft in the control handle.

60. The surgical instrument of claim 53 wherein the positioning element comprises a single control knob extending from the control handle and further using the rotation knob with the dual purpose of being able to firstly rotate the rotation knob to, in turn, rotate the instrument shaft and tool and to secondly pivot the rotation knob to enable the three dimensional positioning.

61. A surgical instrument comprising:
a control handle;
an instrument shaft that extends from the control handle;
a tool disposed from the distal end of the instrument shaft and controlled from the handle as to actuation and positioning thereof;
a distal bendable member for coupling the distal end of the instrument shaft to the tool;
a proximal bendable member for coupling the proximal end of the instrument shaft to the control handle;
cable actuation means extending between the distal and proximal bendable members for coupling motion of the proximal bendable member to the distal bendable member for controlling the positioning of the tool;
and a pivot element mounted by the handle;
a proximal end of the proximal bendable member being mounted to the pivot element for movement therewith;
wherein the pivot element comprises a ball member arranged in an at least partial spherical shaped socket in the handle and capable of three dimensional pivoting therein;
and wherein the socket defines a conical cavity in which the proximal bendable member is pivotable to enable the three dimensional motion.

62. The surgical instrument of claim 61 wherein said control handle has a first section for supporting an actuation element for controlling the actuation of the tool, and a second section for supporting the pivot element used for controlling the positioning of the tool.

63. The surgical instrument of claim 62 wherein the actuation element comprises an actuation lever, a handle control cable controlled from the actuation lever, a pivot mechanism controlled by the handle control cable and a tool actuation cable controlled by the pivot mechanism to control the actuation of the tool.

64. The surgical instrument of claim 63 wherein the pivot mechanism includes a bell crank mechanism and a transfer disc assembly controlled from the bell crank mechanism and for retaining a proximal end of the tool actuation cable.

65. The surgical instrument of claim 60 including a control element extending from the handle and attached to the pivot element for controlling the positioning of the pivot element in three dimensions.

66. The surgical instrument of claim 65 wherein the pivot element comprises a ball and the control element comprises a control knob.

67. The surgical instrument of claim 66 including an actuating lever mounted on the handle for controlling the actuation of the tool, a tool actuation cable and a transfer mechanism mounted between the control knob and the proximal end of the proximal bendable member controlled from the transfer mechanism for actuating the tool actuation cable.

68. The surgical instrument of claim 67 wherein the transfer mechanism comprises a pivot crank and a transfer disc, the actuation lever controlling the pivot crank and the transfer disc controlling the tool actuation cable.

69. The surgical instrument of claim 61 wherein at least one of said bendable members comprise a single unitary slotted structure that is readily capable of bending in any direction and wherein said slotted structure is comprised of a plurality of separately disposed non-contiguous slots.

70. The surgical instrument of claim 61 wherein the pivot element comprises a ball member that has an outer at least partially spherical shaped surface arranged in a spherical shaped socket in the handle and capable of three dimensional pivoting therein.

71. The surgical instrument of claim 70 wherein the socket defines a conical cavity in which the proximal bendable member is pivotable to enable the three dimensional motion.

72. The surgical instrument of claim 71 wherein the proximal end of the proximal bendable member is fixedly supported in the ball member with the distal end of the proximal bendable member extending into the conical cavity and bendable by pivoting of the ball member in the socket.

73. The surgical instrument of claim 72 including a rotation knob rotatably attached to the ball member to control the positioning of the ball member and, in turn, the proximal bendable member.

74. The surgical instrument of claim 72 including a rotation knob attached to the instrument shaft for enabling rotation thereof.

75. The surgical instrument of claim 61 including rotation means adjacent the control handle for rotating the instrument shaft.

76. The surgical instrument of claim 75 wherein the rotation means comprises a rotation knob with the dual purpose of being able to first rotate the rotation knob to, in turn, rotate the instrument shaft and tool and to second pivot the rotation knob in three dimensions to enable the three dimensional positioning of the tool.

77. The surgical instrument of claim 61 including a lock mechanism for fixing the position of the proximal bendable member relative to the control handle.

78. The surgical instrument of claim 77 wherein the lock mechanism comprises a locking lever mounted on the control handle and for selective engagement with the ball member.

79. In a medical instrument having a proximal control handle and a distal tool that are intercoupled by an elongated instrument shaft that is meant to pass internally of an anatomic body, proximal and distal movable members that respectively intercouple said proximal control handle and said distal tool with said instrument shaft, and cable actuation means extending through the proximal and distal bendable members for coupling motion of the proximal bendable member to the distal bendable member, a method of controlling the position of the tool from the handle comprising; rotating a first control member to control the rotational position of the tool, actuating a second control member for locking the position of the tool at a fixed position, constructing the movable members as bendable members, supporting the proximal bendable member in a support member that is disposed within the handle and supporting the second control member between the support member and handle so as to selectively lock the position of the tool.

80. The method of claim 79 including pivoting the first control member in three dimensions to control the positioning of the tool in three dimensions and wherein the rotating of the first control member controls the rotational orientation of the tool by rotating the instrument shaft.

81. The method of claim 79 wherein the step of supporting the proximal bendable member in a support member includes providing a ball and socket and controlling the position of the ball so as to pivot the ball relative to the socket.

82. The method of claim 80 including constructing the first control member as a single control knob.

83. The method of claim 80 including connecting the first control member with the proximal bendable member for rotating the instrument shaft and, in turn, the tool.

84. In a medical instrument having a proximal control handle and a distal tool that are intercoupled by an elongated instrument shaft that is meant to pass internally of an anatomic body, proximal and distal movable members that respectively intercouple said proximal control handle and said distal tool with said instrument shaft, and cable actuation means extending through the proximal and distal bendable members for coupling motion of the proximal bendable member to the distal bendable member, a method of controlling the position of the tool from the handle comprising; rotating a first control member to control the rotational position of the tool, actuating a second control member for locking the position of the tool at a fixed position, providing a ball and socket and controlling the position of the ball so as to pivot the ball relative to the socket, constructing the movable members as bendable members, constructing the first control member as a single control knob and mounting a proximal end of the proximal bendable member in the ball that is supported for three dimensional pivoting in the socket.

85. The method of claim 84 including supporting the second control member between the ball and handle so as to selectively lock the position of the tool.

86. A surgical instrument comprising:
a control handle;
an instrument shaft that extends from the control handle;
a tool disposed from the distal end of the instrument shaft and controlled from the handle as to actuation and positioning thereof;
said control handle having a first section for supporting a first actuation element for controlling the actuation of the tool, and a second section for supporting a second actuation element for controlling the positioning of the tool between locked and unlocked positions;
a distal bendable member for coupling the distal end of the instrument shaft to the tool;
a proximal bendable member for coupling the proximal end of the instrument shaft to the control handle;
cable actuation means extending between the distal and proximal bendable members for coupling motion of the proximal bendable member to the distal bendable member for controlling the positioning of the tool;
a ball and socket structure supported by the control handle responsive to the second actuation element for locking the relative position between the ball and socket;
and means for mounting the proximal end of the proximal bendable member in the ball.

87. The surgical instrument of claim 86 including means for manually controlling the position of the ball in the socket.

88. The surgical instrument of claim 86 wherein said second actuation element includes a locking lever for locking the ball to the socket to hold the position of the tool.

* * * * *